United States Patent
Fukui et al.

(10) Patent No.: US 10,105,313 B2
(45) Date of Patent: Oct. 23, 2018

(54) USES OF ROSE PIGMENT COMPOUNDS

(71) Applicant: SUNTORY HOLDINGS LIMITED, Osaka (JP)

(72) Inventors: Yuko Fukui, Osaka (JP); Yuko Yoshimoto, Osaka (JP); Tatsuo Matsuoka, Osaka (JP); Sayuri Kitagawa, Osaka (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/311,612

(22) PCT Filed: May 19, 2015

(86) PCT No.: PCT/JP2015/064356
§ 371 (c)(1),
(2) Date: Nov. 16, 2016

(87) PCT Pub. No.: WO2015/178385
PCT Pub. Date: Nov. 26, 2015

(65) Prior Publication Data
US 2017/0079904 A1    Mar. 23, 2017

(30) Foreign Application Priority Data
May 19, 2014   (JP) ................ 2014-103299

(51) Int. Cl.
| A61K 8/97 | (2017.01) |
| C09B 61/00 | (2006.01) |
| A61Q 19/00 | (2006.01) |
| A61K 8/60 | (2006.01) |
| A61K 8/49 | (2006.01) |
| A61K 8/19 | (2006.01) |
| A61Q 19/08 | (2006.01) |
| A61K 36/738 | (2006.01) |

(52) U.S. Cl.
CPC .......... *A61K 8/97* (2013.01); *A61K 8/19* (2013.01); *A61K 8/498* (2013.01); *A61K 8/602* (2013.01); *A61K 36/738* (2013.01); *A61Q 19/00* (2013.01); *A61Q 19/08* (2013.01); *C09B 61/00* (2013.01); *A61K 2800/43* (2013.01); *A61K 2800/58* (2013.01)

(58) Field of Classification Search
CPC .......... A61K 8/97; A61K 8/602; A61K 8/498; A61K 8/19; A61K 36/738; A61K 2800/58; A61K 2800/43; C09B 61/00; A61Q 19/00; A61Q 19/08
See application file for complete search history.

(56) References Cited

U.S. PATENT DOCUMENTS

| 2010/0303872 A1 | 12/2010 | Dumas et al. |
| 2012/0011771 A1 | 1/2012 | Fukui et al. |

FOREIGN PATENT DOCUMENTS

| JP | 2002201372 A | 7/2002 |
| JP | 2003012489 A | 1/2003 |
| JP | 3487739 B2 | 1/2004 |
| JP | 2004067552 A | 3/2004 |
| JP | 3532244 B2 | 5/2004 |
| JP | 4233734 B2 | 3/2009 |
| JP | 2011021001 A | 2/2011 |
| JP | 2011236147 A | 11/2011 |
| WO | WO-2010110382 A1 | 9/2010 |

OTHER PUBLICATIONS

EP Application 15795780.4—Extended European Search Report dated Oct. 16, 2017.
Yuko Fukui, et al., "Structure of rosacyanin B, a novel pigment from the petals of *Rosa hybrida*", Tetrahedron Letters, Apr. 1, 2002, vol. 43, No. 14, pp. 2637-2639.
Yuko Fukui, et al., "Two novel blue pigments with ellagitannin moiety, rosacyanins A1 and A2, isolated from the petals of *Rosa hybrida*", Tetrahedron, Oct. 9, 2006, vol. 62, No. 41, pp. 9661-9670.
Yukihisa Katsumoto, et al., "Engineering of the Rose Flavonoid Biosynthetic Pathway Successfully Generated Blue-Hued Flowers Accumulating Delphinidin", Plant Cell Physiology, Nov. 1, 2007, 48(11), pp. 1589-1600.
Christine A. Williams, et al., "Anthocyanins and other flavonoids", Natural Product Reports, Jan. 1, 2004, vol. 21, No. 4, pp. 539-573.
Timothy A. Holton, et al., "Blue roses—a pigment of our imagination?", Trends in Biotechnology, Feb. 1, 1994, vol. 12, No. 2, pp. 40-42.
PCT/JP2015/064356—International Search Report dated Aug. 18, 2015.
Hiroshi Tanaka, Fragrance Journal, 1998, vol. 26, No. 4, pp. 43-48.

*Primary Examiner* — Jonathan S Lau
(74) *Attorney, Agent, or Firm* — Drinker Biddle & Reath LLP

(57) ABSTRACT

An object of the present invention is to provide hyaluronidase inhibitors, collagenase inhibitors, elastase inhibitors, MMP-1 production suppressors, and collagen synthesis promoters that contain as an active component one or more pigment compounds that are obtained as extracted from plants of the family Rosaceae, as well as agents for cutaneous application, skin cosmetics, and quasi-drugs that contain such pigment compounds. The present invention provides hyaluronidase inhibitors, collagenase inhibitors, elastase inhibitors, MMP-1 production suppressors, collagen synthesis promoters, agents for cutaneous application, skin cosmetics, and quasi-drugs that contain one or more compounds in a class of rosacyanins or one or more compounds in a class of rosadelphins as an active component.

30 Claims, 1 Drawing Sheet

USES OF ROSE PIGMENT COMPOUNDS

This application is the National Stage of International Application No. PCT/JP2015/064356, filed May 19, 2015, and claims benefit of Japanese Application No. 2014-103299 filed on May 19, 2014.

TECHNICAL FIELD

The present invention relates to hyaluronidase inhibitors, collagenase inhibitors, elastase inhibitors, MMP-1 production suppressors, collagen synthesis promoters, agents for cutaneous application, skin cosmetics, and quasi-drugs that contain as an active component those polyphenol compounds which are obtained from plants of the rose family (Rosaceae), in particular, blue- or mauve-hued roses, or Rosaceae having a gene encoding flavonoid 3',5'-hydroxylase. The present invention particularly relates to hyaluronidase inhibitors, collagenase inhibitors, elastase inhibitors, MMP-1 production suppressors, collagen synthesis promoters, agents for cutaneous application, skin cosmetics, and quasi-drugs that contain one or more compounds in a class of rosacyanins or one or more compounds in a class of rosadelphins as an active component.

BACKGROUND ART

When skin's metabolism or sebaceous gland function declines due, for example, to aging or stress, the skin becomes susceptible to external stimuli and develops various symptoms. For example, drying may increase the chance for feeling itchy. In addition, if the skin's fibrous component withers under exposure to ultraviolet rays, wrinkling and other symptoms will develop.

Skin aging such as wrinkle formation or reduced elasticity may occur due to various causes including fiber reduction, degeneration and regression of dermis matrices such as collagen and elastin.

The skin's dermis and epidermis are composed of cutaneous tissues comprising epidermal cells, fibroblast cells and extracellular matrices such as elastin and collagen that are outside those cells to support the skin structure. If the skin is young, the interactions of these cutaneous tissues keep homeostasis by which water retention, softness/flexibility, elasticity and other properties are ensured and apparently, the skin has resilience and glow and is maintained in a fresh condition. However, on account of external factors such as UV radiation, significant drying of the air, excessive skin washing and stress, as well as aging, elastin as a major constituent of the extracellular matrices will decompose or degenerate whereas collagen is not only produced in a smaller amount but also crosslinked to become less elastic. Consequently, the moisturizing function and elasticity of the skin decrease and the horny layer begins to shed off abnormally, whereupon the skin will lose its resilience and glow, eventually developing various symptoms including roughness, wrinkles, and dullness.

Plants of the family Rosaceae are quite diverse and among their varieties roses that are classified in the genus *Rosa* and which are utilized as flowers and ornamental plants are said to include as many as 3000 species, most of which are cultivars created by crossing and other conventional breeding methods. The hybrid cultivars are roughly classified into two types, Old Garden Rose and Modern Rose (Patent Document 1).

Pigments in roses have been investigated in detail. Take, for example, anthocyanin pigments which are known to include cyanidin 3,5-diglucoside, pelargonidin 3,5-diglucoside, cyaniding 3-glucoside, pelargonidin 3-glucoside, peonidin 3,5-diglucoside, and peonidin 3-glucoside. Also known are many carotenoid compounds that develop a yellow color. These pigments are simultaneously accumulated in flowers and ornamental plants which hence develop a red or yellow color.

"Madame Violet", a mauve-hued rose variety, is known to contain rosacyanins as blue color pigment compounds (compounds I-III) (Patent Document 2). It is also known that the rose variety "APPLAUSE (registered trademark)" (or Suntory Blue Rose APPLAUSE (trademark)") contains rosadelphins (compounds IV-VI) (Patent Document 3). These compounds have been characterized in terms of their structures, colors and various spectral data but their physiological activities and functionality are yet to be clarified.

Components in plants of the family Rosaceae have been reported to have various activity including antiallergic activity, skin lightening activity (melanin production suppressing activity or tyrosinase inhibiting activity), moisturizing activity, and antioxidizing activity. A patent document (Patent Document 4) discloses that extracts of *Rosa hybrida* and *Rosa laevigata* are effective as agents for suppressing mucopolysaccharide fragmentation. Another patent document (Patent Document 5) discloses that essences of plants of the family Rosaceae are effective as cosmetics for sensitive skin. Still another patent document (Patent Document 6) discloses that an extract of *Rosa Centifolia* is effective as a whitening agent for cutaneous application. To benefit from these effects of components derived from plants of the family Rosaceae, extracts and petals of roses called Old Garden Rose (of the genus *Rosa*) including *Rosa Centifolia, Rosa Damascena*, and *Rosa Gallica* have heretofore been used as agents for cutaneous application (e.g. cosmetics), bath salts, and flavors in foods or beverages. However, these rose varieties which have been used for non-ornamental purposes lack the aforementioned rosacyanins and rosadelphins.

CITATION LIST

Patent Literature

Patent Document 1: JP 2011-236147 A
Patent Document 2: JP 2002-201372 A
Patent Document 3: WO 2010/110382 A1
Patent Document 4: Japanese Patent No. 3532244
Patent Document 5: Japanese Patent No. 3487739
Patent Document 6: Japanese Patent No. 4233734

SUMMARY OF INVENTION

Technical Problem

An object of the present invention is to provide hyaluronidase inhibitors, collagenase inhibitors, elastase inhibitors, MMP-1 production suppressors, and collagen synthesis promoters that contain as an active component the tannin and other polyphenol compounds that are obtained by extraction from plants of the family Rosaceae, as well as agents for cutaneous application, skin cosmetics, and quasi-drugs that contain those pigment compounds.

Solution to Problem

To attain the above-mentioned object, the present inventors conducted intensive studies and consequently found that rosacyanins which are pigments discovered from the petals of mauve-hued roses as well as rosadelphins which are pigments synthesized in roses having the flavonoid 3',5'-hydroxylase gene (F3'5'H gene) exhibited strong hyaluronidase inhibiting activity, collagenase inhibiting activity, elastase inhibiting activity, MMP-1 production suppressing activity, and collagen synthesis promoting activity. The present inventors also found that extracts of plants of the family Rosaceae containing rosacyanins or rosadelphins exhibited stronger hyaluronidase inhibiting, collagenase inhibiting, and elastase inhibiting activities than extracts of the conventional plants of the family Rosaceae which contain neither rosacyanins nor rosadelphins; the present invention has been accomplished on the basis of these findings.

Thus, the present invention relates to the following.

[1] A hyaluronidase inhibitor containing as an active component one or more compounds selected from the group consisting of a compound in a class of rosacyanins as represented by the following general formula (I):

[Formula 1]

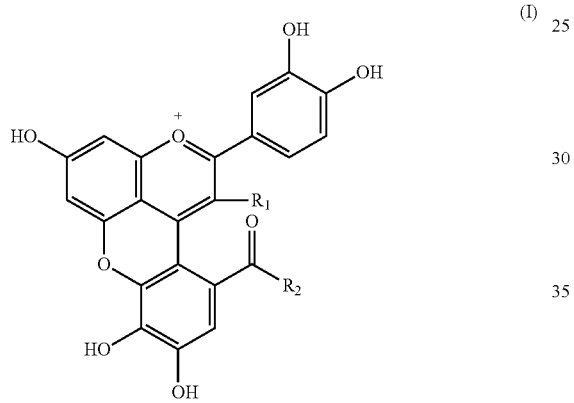

(I)

[where $R_1$ and $R_2$, taken together, form —O—; or alternatively, $R_1$ is the following group (a):

[Formula 2]

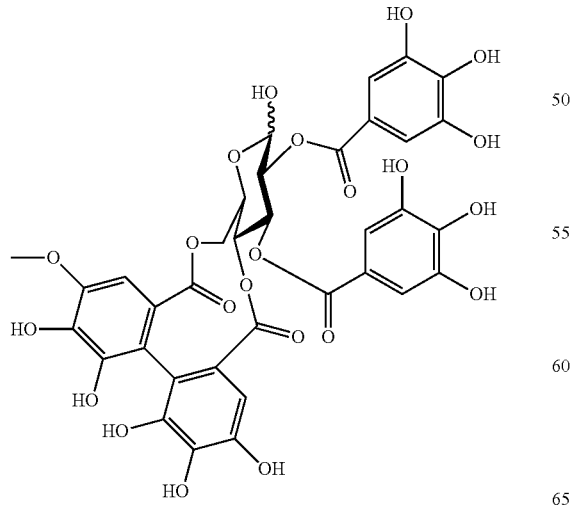

{provided that in group (a), the coordination (wavy line) to the hydroxyl group at position 1 of glucose indicates tautomerism of α- and β-forms} or the following group (b):

[Formula 3]

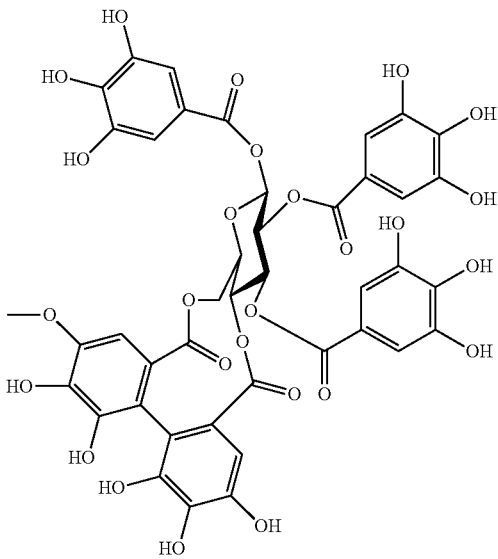

and $R_2$ is —OH]; and a compound in a class of rosadelphins as represented by the following general formula (II):

[Formula 4]

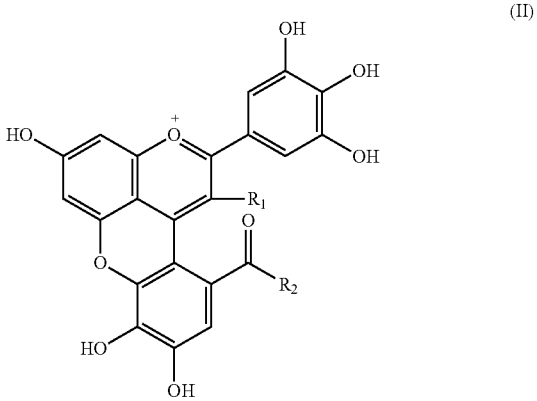

(II)

{where R₁ is the following formula (a):

[Formula 5]

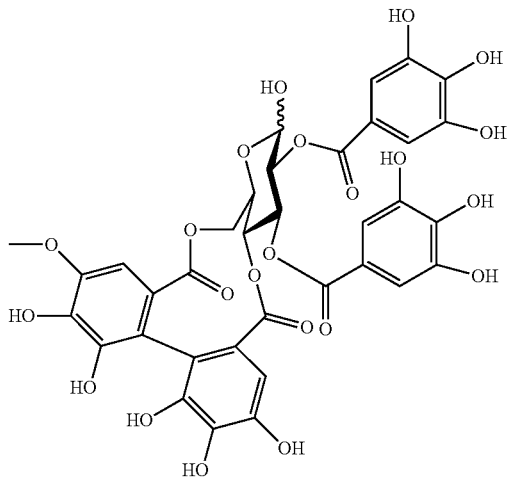

{provided that in group (a), the coordination (wavy line) to the hydroxyl group at position 1 of glucose indicates tautomerism of α- and β-forms} and R₂ is —OH; or R₁ and R₂, taken together, form —O—; or R₁ is the following group (b):

[Formula 6]

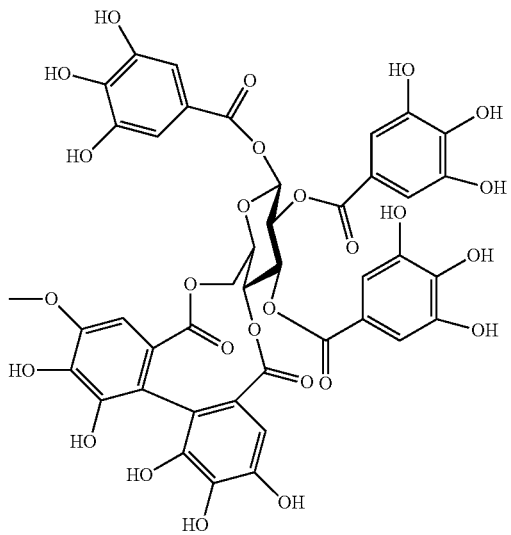

and R₂ is —OH}.

[2] A collagenase inhibitor containing as an active component one or more compounds selected from the group consisting of a compound in a class of rosacyanins as represented by the following general formula (I):

[Formula 7]

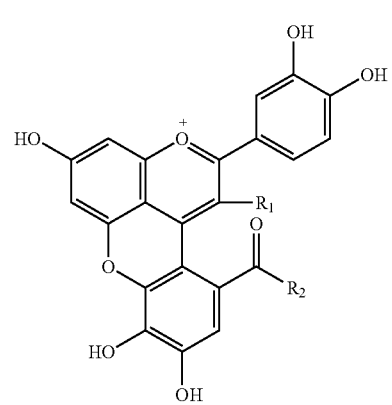

[where R₁ and R₂, taken together, form —O—; or alternatively, R₁ is the following group (a):

[Formula 8]

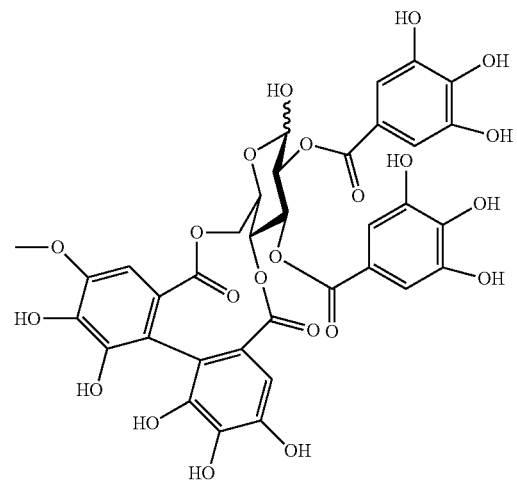

{provided that in group (a), the coordination (wavy line) to the hydroxyl group at position 1 of glucose indicates tautomerism of α- and β-forms} or the following group (b):

[Formula 9]

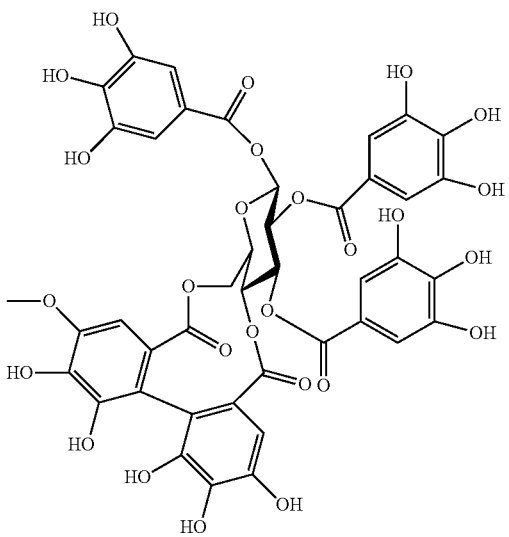

and $R_2$ is —OH] and
a compound in a class of rosadelphins as represented by the following general formula (II):

[Formula 10]

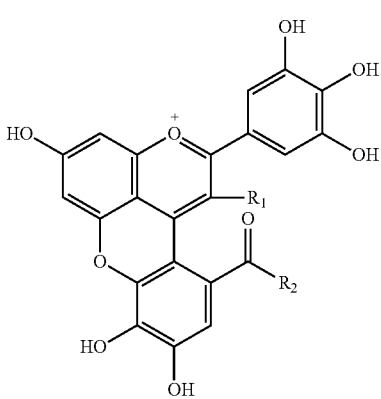
(II)

{where $R_1$ is the following formula (a):

[Formula 11]

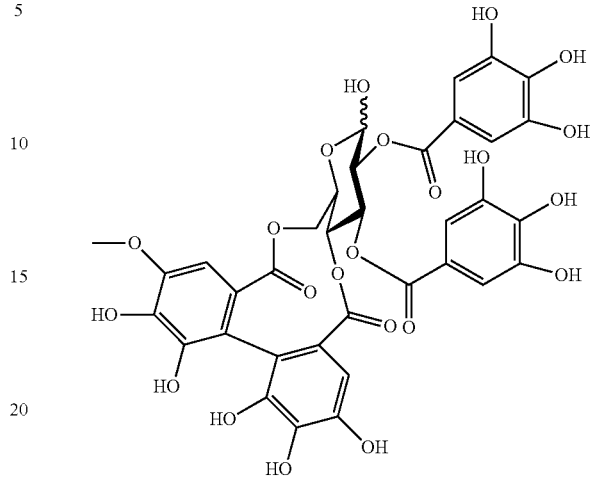

{provided that in group (a), the coordination (wavy line) to the hydroxyl group at position 1 of glucose indicates tautomerism of α- and β-forms} and $R_2$ is —OH; or $R_1$ and $R_2$, taken together, form —O—; or $R_1$ is the following group (b):

[Formula 12]

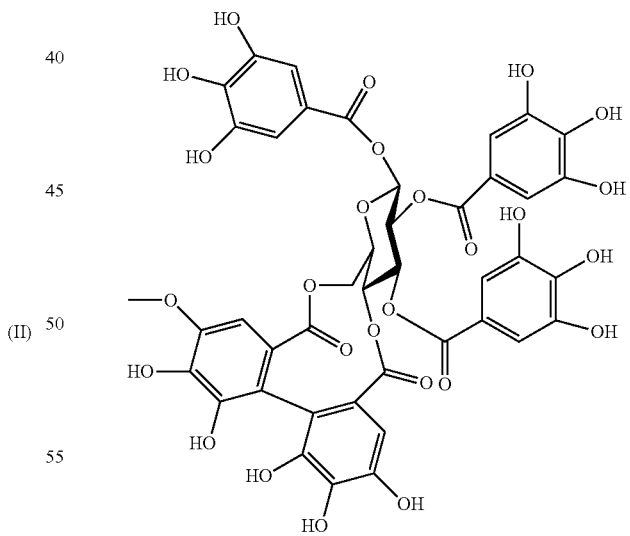

and $R_2$ is —OH}.

[3] An elastase inhibitor containing as an active component one or more compounds selected from the group consisting of a compound in a class of rosacyanins as represented by the following general formula (I):

[Formula 13]

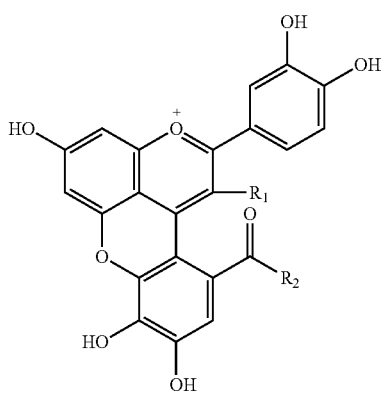
(I)

[where $R_1$ and $R_2$, taken together, form —O—; or alternatively, $R_1$ is the following group (a):

[Formula 14]

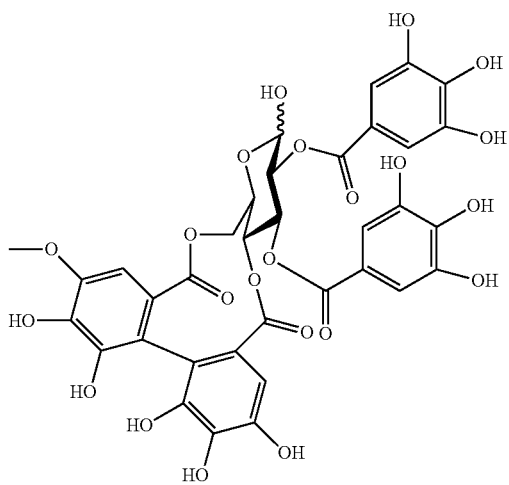

{provided that in group (a), the coordination (wavy line) to the hydroxyl group at position 1 of glucose indicates tautomerism of α- and β-forms} or the following group (b):

[Formula 15]

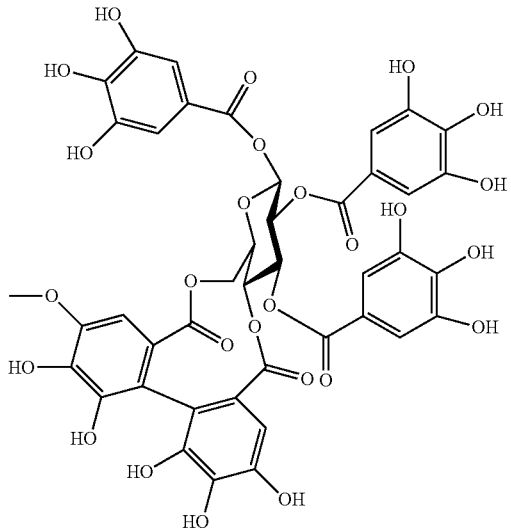

and $R_2$ is —OH] and a compound in a class of rosadelphins as represented by the following general formula (II):

[Formula 16]

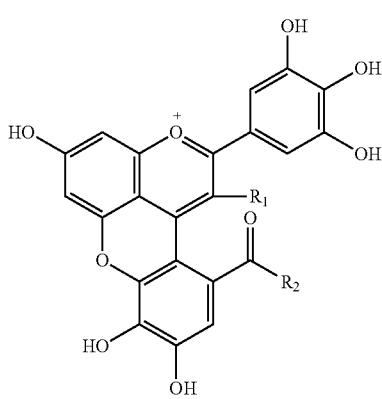
(II)

{where $R_1$ is the following formula (a):

[Formula 17]

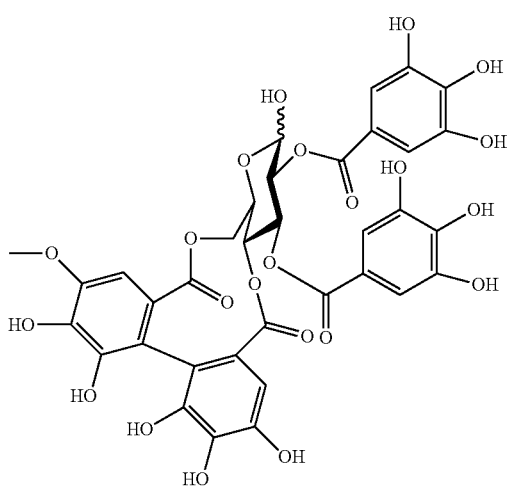

{provided that in group (a), the coordination (wavy line) to the hydroxyl group at position 1 of glucose indicates tautomerism of α- and β-forms} and $R_2$ is —OH; or $R_1$ and $R_2$, taken together, form —O—; or $R_1$ is the following group (b):

[Formula 18]

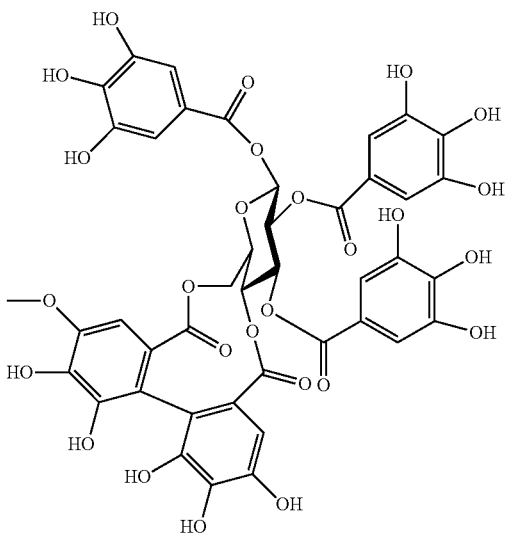

and $R_2$ is —OH}.

[4] The hyaluronidase inhibitor, collagenase inhibitor or elastase inhibitor as recited in any one of [1] to [3], wherein the compound in a class of rosacyanins is one or more compounds selected from the group consisting of rosacyanin A1 represented by the following formula:

[Formula 19]

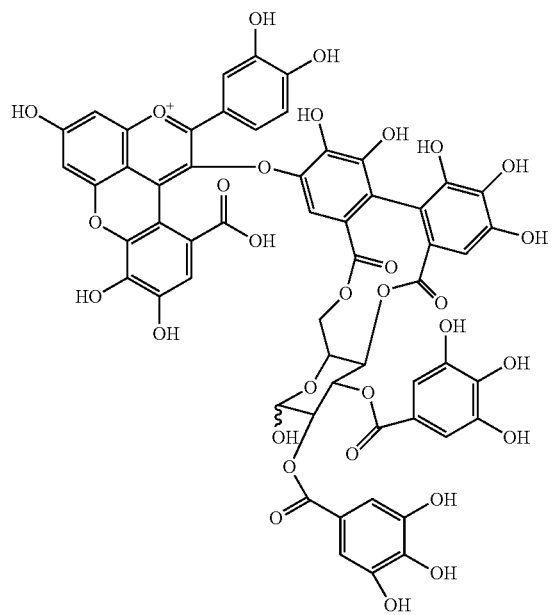

{provided that in this group, the coordination (wavy line) to the hydroxyl group at position 1 of glucose indicates tautomerism of α- and β-forms}, rosacyanin A2 represented by the following formula:

[Formula 20]

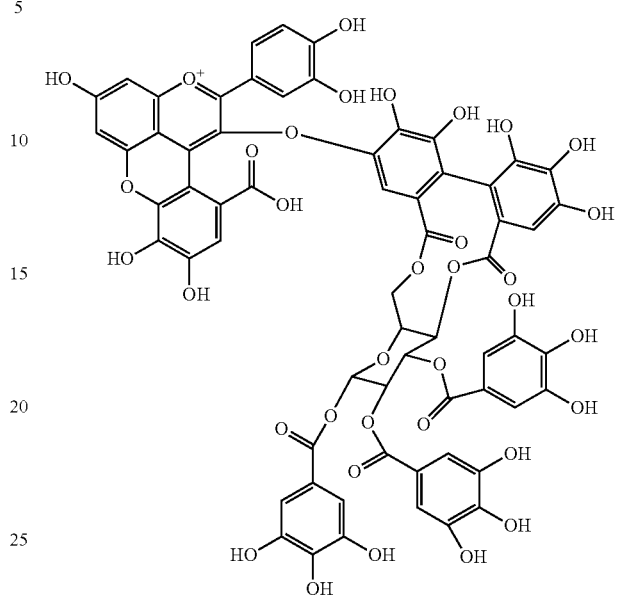

and rosacyanin B represented by the following formula:

[Formula 21]

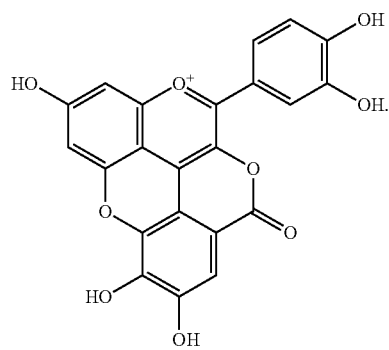

[5] The hyaluronidase inhibitor, collagenase inhibitor or elastase inhibitor as recited in any one of [1] to [4], which contains an extract of a plant of the family Rosaceae that contains the compound in a class of rosacyanins.

[6] The hyaluronidase inhibitor, collagenase inhibitor or elastase inhibitor as recited in [5], wherein the plant of the family Rosaceae that contains the compound in a class of rosacyanins is one or more plants of the family Rosaceae as selected from the group consisting of Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver.

[7] The hyaluronidase inhibitor, collagenase inhibitor or elastase inhibitor as recited in any one of [1] to [6], wherein the compound in a class of rosadelphins is one or more compounds selected from the group consisting of rosadelphin A1 represented by the following formula:

[Formula 22]

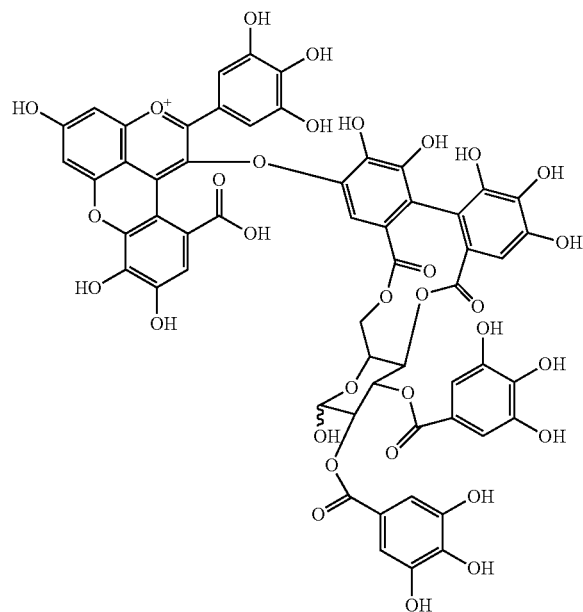

{provided that in this group, the coordination (wavy line) to the hydroxyl group at position 1 of glucose indicates tautomerism of α- and β-forms}, rosadelphin A2 represented by the following formula:

[Formula 23]

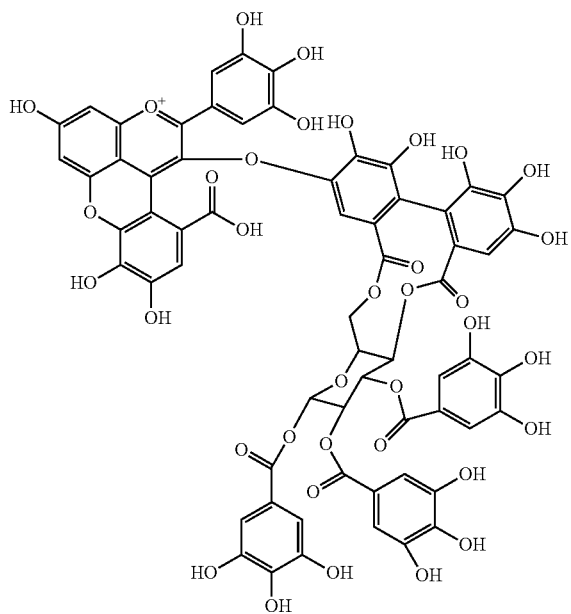 [SMILES: O=C(OC1OC2COC(=O)c3cc(Oc4c(-c5ccc(O)c(O)c5)[o+]c5cc(O)cc6c5c4-c4c(C(=O)O)cc(O)c(O)c4O6)c(O)c(O)c3-c3c(cc(O)c(O)c3O)C(=O)OC2C(OC(=O)c2cc(O)c(O)c(O)c2)C1OC(=O)c1cc(O)c(O)c(O)c1)c1cc(O)c(O)c(O)c1]

and rosadelphin B represented by the following formula:

[Formula 24]

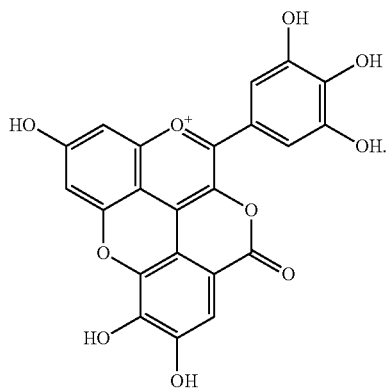

[8] The hyaluronidase inhibitor, collagenase inhibitor or elastase inhibitor as recited in any one of [1] to [7], which contains an extract of a plant of the family Rosaceae that contains the compound in a class of rosadelphins.

[9] The hyaluronidase inhibitor, collagenase inhibitor or elastase inhibitor as recited in [8], wherein the plant of the family Rosaceae that contains the compound in a class of rosadelphins is a plant of the family Rosaceae that contains the flavonoid 3',5'-hydroxylase gene.

[10] The hyaluronidase inhibitor, collagenase inhibitor or elastase inhibitor as recited in [9], wherein the plant of the family Rosaceae that contains the compound in a class of rosadelphins is APPLAUSE (registered trademark).

[11] The hyaluronidase inhibitor, collagenase inhibitor or elastase inhibitor as recited in [9], wherein the plant of the family Rosaceae that contains the compound in a class of rosadelphins is Suntory Blue Rose APPLAUSE (trademark).

[12] An agent for cutaneous application which contains the hyaluronidase inhibitor, collagenase inhibitor or elastase inhibitor as recited in any one of [1] to [11].

[13] A skin cosmetic which contains the hyaluronidase inhibitor, collagenase inhibitor or elastase inhibitor as recited in any one of [1] to [11].

[14] A quasi-drug which contains the hyaluronidase inhibitor, collagenase inhibitor or elastase inhibitor as recited in any one of [1] to [11].

[15] An agent for cutaneous application which contains as an active component one or more of the compounds selected from the group consisting of the compound in a class of rosacyanins and the compound in a class of rosadelphins as defined in any one of [1] to [4] and [7], or the extract as defined in any one of [5], [6] and [8] to [11].

[16] A skin cosmetic which contains as an active component one or more compounds selected from the group consisting of the compound in a class of rosacyanins and the compound in a class of rosadelphins as defined in any one of [1] to [4] and [7], or the extract as defined in any one of [5], [6] and [8] to [11].

[17] A quasi-drug which contains as an active component one or more compounds selected from the group consisting of the compound in a class of rosacyanins and the compound in a class of rosadelphins as defined in any one of [1] to [4] and [7], or the extract as defined in any one of [5], [6] and [8] to [11].

[18] An MMP-1 production suppressor which contains as an active component one or more compounds selected from the group consisting of the compound in a class of rosacyanins and the compound in a class of rosadelphins as defined in any one of [1] to [4] and [7], or the extract as defined in any one of [5], [6] and [8] to [11].

[19] A collagen synthesis promoter which contains as an active component one or more compounds selected from the group consisting of the compound in a class of rosacyanins and the compound in a class of rosadelphins as defined in any one of [1] to [4] and [7], or the extract as defined in any one of [5], [6] and [8] to [11].

Advantageous Effects of Invention

The present invention provides novel uses of pigment compounds, the rosacyanins (compounds which exist in mauve- or blue-hued plants of the family Rosaceae, and pigment compounds, the rosadelphins (compounds IV-VI), which exist in plants of the family Rosaceae that have the flavonoid 3′,5′-hydroxylase gene (F3′5′H gene). Extracts obtained from these plants, pigment containing fractions of the extracts, as well as purified forms of the rosacyanins (compounds I-III) and rosadelphins (compounds IV-VI), when compared with the conventionally known extracts of plants of the family Rosaceae and the tannins contained in the extracts, were surprisingly high in hyaluronidase inhibiting activity (about four times as much), and in collagenase inhibiting activity (about twice as much) per polyphenol content; as for elastase inhibiting activity, rosacyanin A1 and rosadelphin A1 showed strong activity but tellimagrandin 1 (TG1) showed little activity. Thus, the present invention provides hyaluronidase inhibitors, collagenase inhibitors, and elastase inhibitors that have superior activities. In addition, the above-described extracts, fractions, compounds in a class of rosacyanins, and compounds in a class of rosadelphins also display superior effects for suppressing MMP-1 production and promoting collagen synthesis (especially promoting synthesis of collagen type I), thus making it possible to provide MMP-1 production suppressors and collagen synthesis promoters.

The present invention also provides agents for cutaneous application, skin cosmetics, and quasi-drugs that contain the above-described pigment compounds. Containing those pigment compounds as an active component, the agents for cutaneous application, skin cosmetics, and quasi-drugs of the present invention contribute to retaining the moisture of the skin tissues as well as maintaining and improving the skin's softness/flexibility and elasticity, thus proving effective for preventing and ameliorating the drying, wrinkling and sagging of the skin. The amounts of ingredients that can be added to cosmetics and other preparations are limited from a stability viewpoint but the pigment compounds for use in the agents for cutaneous application, skin cosmetics, and quasi-drugs of the present invention offer high degree of effectiveness in quantities that can be incorporated in such agents for cutaneous application, skin cosmetics, and quasi-drugs.

Previous studies have revealed the structural formulas of rosacyanins and rosadelphins but nothing has been known about the physiological functions of these pigments for the case where they are contained in plants other than those of the family Rosaceae. By the present invention, these groups of pigment compounds have been found to possess new functionality, so they can be used to prevent and ameliorate the drying, wrinkling and sagging of the skin, thus contributing to improving people's QOL.

DESCRIPTION OF EMBODIMENTS

Figure 1:
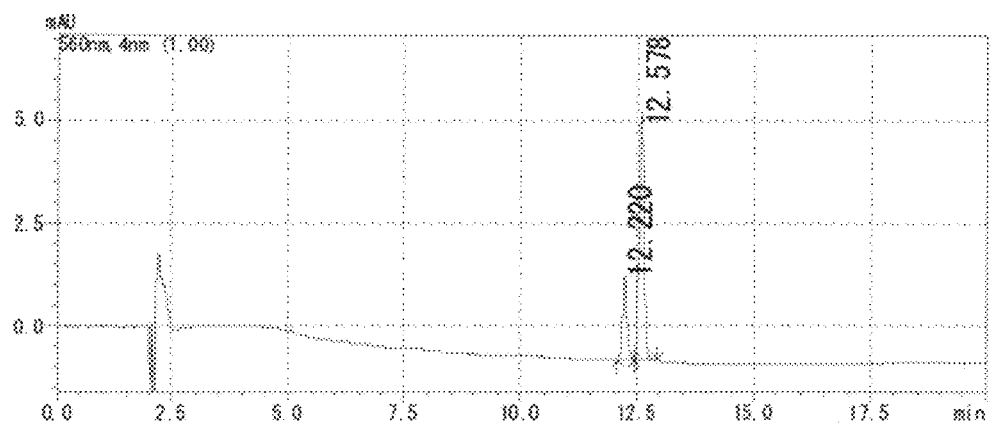
FIG. 1 shows the result of analysis (absorbance at 560 nm) of rosadelphin A1 as purified through a Polymer C18 column.

The present invention relates to hyaluronidase inhibitors, collagenase inhibitors, elastase inhibitors, MMP-1 production suppressors, collagen synthesis promoters, agents for cutaneous application, skin cosmetics, and quasi-drugs that contain one or more compounds in a class of rosacyanins or one or more compounds in a class of rosadelphins as an active component.

(Compounds in a Class of Rosacyanins)

Compounds in a class of rosacyanins that can be used in the present invention may be of any type that has the structure described above; in particular, one or more compounds selected from the group consisting of rosacyanin A1, rosacyanin A2, and rosacyanin B may be used with advantage.

Compounds in a class of rosacyanins may be extracted from plants of the family Rosaceae that develop blue- or mauve-hued colors, say, such varieties as Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver by methods such as those disclosed in JP 2002-201372 A.

(Compounds in a Class of Rosadelphins)

Compounds in a class of rosadelphins that can be used in the present invention may be of any type that has the structure described above; in particular, one or more compounds selected from the group consisting of rosadelphin A1, rosadelphin A2, and rosadelphin B may be used with advantage.

Compounds in a class of rosadelphins do not exist in roses of wild species; in roses into which the flavonoid 3′,5′-hydroxylase gene has been introduced by gene recombination or other techniques or in roses having the flavonoid 3′,5′-hydroxylase gene that are obtained from gene recombinant roses as their parents, the blue pigment delphnidin is synthesized, to which gallates or tellimagradins bind to produce compounds in a class of rosadelphins.

Compounds in a class of rosadelphins can be extracted, typically by the methods disclosed in WO 2010/110382 A1, from the roses into which the flavonoid 3′,5′-hydroxylase gene has been introduced by gene recombination or other techniques or from the roses having the flavonoid 3′,5′-hydroxylase gene that are obtained from the gene recombinant roses as their parents.

(Extracts of Plants of the Family Rosaceae Containing Compounds in a Class of Rosacyanins or Compounds in a Class of Rosadelphins)

In one mode, the present invention relates to hyaluronidase inhibitors, collagenase inhibitors, elastase inhibitors, MMP-1 production suppressors, collagen synthesis promoters, agents for cutaneous application, skin cosmetics, and quasi-drugs that contain extracts of plants of the family Rosaceae containing compounds in a class of rosacyanins or compounds in a class of rosadelphins. These may contain compounds in a class of rosacyanins or compounds in a class of rosadelphins as well as the extracts. Compounds in a class of rosacyanins are preferably one or more compounds selected from the group consisting of rosacyanin A1, rosacyanin A2, and rosacyanin B. And compounds in a class of rosadelphins are one or more compounds selected from the group consisting of rosadelphin A1, rosadelphin A2, and rosadelphin B. In a preferred mode, the extracts contain all of rosadelphin A1, rosadelphin A2, and rosadelphin B.

The extracts of plants of the family Rosaceae that are to be used in the present invention and which contain compounds in a class of rosacyanins can be obtained by methods well known to the skilled artisan from plants of the family Rosaceae that develop blue- or mauve-hued colors, say, such varieties as Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver.

The extracts of plants of the family Rosaceae that are to be used in the present invention and which contain compounds in a class of rodelphins can be obtained by methods well known to the skilled artisan from the roses into which the flavonoid 3',5'-hydroxylase gene has been introduced by gene recombination or other techniques or from the roses having the flavonoid 3',5'-hydroxylase gene that are obtained from the gene recombinant roses as their parents, for example, varieties such as APPLAUSE (registered trademark). APPLAUSE (registered trademark) refers to the same variety as Suntory Blue Rose APPLAUSE (trademark) which is available from Suntory Flowers Co., Ltd. (Tokyo, Japan).

The extracts of plants of the family Rosaceae containing compounds in a class of rosacyanins or compounds in a class of rosadelphins can specifically be obtained by the methods that are described in Examples and which are outlined below.

To obtain the extracts for use in the present invention, the petal parts of the roses mentioned above are preferably used but in addition to the petals, the calyxes and pollen may also be contained. Extracts of the flower parts of the roses mentioned above may also be used in the present invention. Flowers as cut from the stem or their petals may be immediately subjected to extraction or, alternatively, flowers or petals in a frozen or dried state may be employed. To enhance the extraction efficiency, flowers or petals are preferably crushed or otherwise ground into fragments as appropriate before they are used in the production of extracts. The methods of producing extracts are not particularly limited and may include immersing the flowers or petals of the roses mentioned above in an extraction solvent or heating an extraction solvent under reflux as it contains the flowers or petals.

In the case of producing the extracts by immersing the above-described flowers or petals in an extraction solvent, the amount of the extraction solvent to be used is not particularly limited and may range, for example, from 1 to 30 times the weight of the flowers or petals on a weight basis. The immersion time is not particularly limited, either, and it may range, for example, from 0.25 to 72 hours. The immersion temperature also is not particularly limited and may range, for example, from 1 to 100° C. Preferred extraction solvents are water, lower alcohols, and aqueous solutions of lower alcohols. Lower alcohols that can be used are ones having 1 to 5 carbon atoms, such as monohydric alcohols, dihydric alcohols, and trihydric alcohols; specific examples that can be used are known lower alcohols including methyl alcohol, ethyl alcohol, propyl alcohol, butyl alcohol, pentyl alcohol, glycerol, propylene glycol, 1,3-butylene glycol, 1,3-propanediol, and pentylene glycol. The concentration of lower alcohols is not limited and aqueous solutions that contain lower alcohols in 5 to 90 wt % of their total amount may be used. Particularly preferred extraction solvents include an aqueous ethanol or acetonitrile or 1,3-butylene glycol solution that contain the organic solvent in 5 to 90 wt % of their total amount. To prevent the decomposition of the pigment compounds, extraction is preferably carried out under acidic conditions. The acidic conditions are not particularly limited and it is preferred to use pH 1-6 and acids such as the citric acid, hydrochloric acid, phosphoric acid, citric acid, lactic acid, tartaric acid and ascorbic acid that are specified in the Standards for the Ingredients of Quasi-Drugs and which are approved for use in the manufacture of cosmetics, as well as the food additive acetates and sulfates.

The same extraction solvents as described above may be employed in the case of manufacturing the extract by the method in which they are heated under reflux as they contain the flowers or petals of the roses mentioned above.

After extraction, any suitable means such as filtration or centrifugation may be used to separate the extract from the residual flowers or petals.

The extract obtained may be used in the intended applications of the present invention either as such or as a concentrate from which the extraction solvent has been removed appropriately or as a dilution of the extract per se or its concentrate. To remove acids from the obtained extract so that its pH is reverted to neutrality, it is desired that the extract is adsorbed on an adsorbent resin such as Diaion (trademark) HP-20 (Mitsubishi Chemical Corporation) or Diaion (trademark) HP 2MG (Mitsubishi Chemical Corporation), followed by washing off the acids with water and recovering the necessary fractions with a solvent. Alternatively, the extract obtained may be partially or thoroughly purified in accordance with standard methods and the resulting purified product may also be used in the intended applications of the subject application as extracts of plants of the family Rosaceae that contain compounds in a class of rosacyanins or compounds in a class of rosadelphins. The extracts of the present invention, concentrates or dilutions thereof may be used in a liquid state or, alternatively, they may be spray-dried, freeze-dried, vacuum-dried or otherwise dried before they are used as such or after being reduced to a powder or granulated.

For the method by which to confirm the fact that the extracts contain compounds in a class of rosacyanins or compounds in a class of rosadelphins, see Examples described below.

(Hyaluronidase Inhibitors, Collagenase Inhibitors, Elastase Inhibitors, MMP-1 Production Suppressors, and Collagen Synthesis Promoters)

The hyaluronidase inhibitors, collagenase inhibitors, elastase inhibitors, MMP-1 production suppressors, or collagen synthesis promoters of the present invention contain compounds in a class of rosacyanins or compounds in a class of rosadelphins. In addition, the hyaluronidase inhibitors, collagenase inhibitors, elastase inhibitors, MMP-1 production suppressors, or collagen synthesis promoters of the present invention may contain one or more compounds selected from the group consisting of compounds in a class of rosacyanins and compounds in a class of rosadelphins. Further in addition, extracts of plants of the family Rosaceae containing compounds in a class of rosacyanins, extracts of plants of the family Rosaceae containing compounds in a class of rosadelphins, or combinations of these extracts may be immediately used as the hyaluronidase inhibitors, collagenase inhibitors, elastase inhibitors, MMP-1-1 production suppressors, or collagen synthesis promoters of the present invention.

The hyaluronidase inhibitors, collagenase inhibitors, elastase inhibitors, MMP-1 production suppressors, or collagen synthesis promoters of the present invention may be formulated with pharmacologically acceptable carriers or additives incorporated to such an extent that they will not impair the intended effects of the compounds in a class of rosacyanins and the compounds in a class of rosadelphins, as well as the extracts of plants of the family Rosaceae containing the compounds in a class of rosacyanins and the compounds in a class of rosadelphins. Exemplary carriers include water, physiological saline, ethanol, propylene glycol, glycerin, 1,3-butylene glycol, etc. Exemplary additives include glucose, sucrose, lactose, dextrin, cyclodextrin, etc. In addition, excipients, emulsifiers, isotonization agents (tonicity agents), buffers, solvent promoters, antiseptics, stabilizers, antioxidants and the like that are commonly used in formulating procedures may also be incorporated as appropriate.

The formulated hyaluronidase inhibitors, collagenase inhibitors, elastase inhibitors, MMP-1 production suppressors, or collagen synthesis promoters of the present invention may take on any dosage forms such as liquid, paste, gel, powder, and granular forms.

The contents of the active components in the hyaluronidase inhibitors, collagenase inhibitors, elastase inhibitors, MMP-1 production suppressors, or collagen synthesis promoters of the present invention, namely, the compounds in a class of rosacyanins, the compounds in a class of rosadelphins, the extracts of plants of the family Rosaceae containing compounds in a class of rosacyanins, and the extracts of plants of the family Rosaceae containing compounds in a class of rosadelphins, may be determined in any desired way by considering the aspect of effects.

(Agents for Cutaneous Application, Skin Cosmetics, and Quasi-Drugs)

By containing the compounds in a class of rosacyanins or the compounds in a class of rosadelphins, the agents for cutaneous application, skin cosmetics, and quasi-drugs of the present invention are capable of preventing or ameliorating the drying, wrinkling and sagging of the skin in an effective manner. The agents for cutaneous application, skin cosmetics, and quasi-drugs of the present invention may be those which contain one or more compounds as selected from the group consisting of compounds in a class of rosacyanins, compounds in a class of rosadelphins, and combinations of compounds in a class of rosacyanins and compounds in a class of rosadelphins. Further in addition, the agents for cutaneous application, skin cosmetics, and quasi-drugs of the present invention may be those which contain the extracts of plants of the family Rosaceae containing compounds in a class of rosacyanins, the extracts of plants of the family Rosaceae containing compounds in a class of rosadelphins, or combinations of these extracts.

The agents for cutaneous application, skin cosmetics, and quasi-drugs of the present invention may further incorporate, as appropriate, those components which are commonly used in agents for cutaneous application, skin cosmetics, and quasi-drugs, including carriers such as aqueous solvents, alcohols, oils and fats, waxes, etc., and additives such as excipients, emulsifiers, isotonization agents (tonicity agents), buffers, diluents, solvent promoters, antiseptics, stabilizers, antioxidants, etc.

The agents for cutaneous application, skin cosmetics, and quasi-drugs of the present invention may take on any dosage forms such as powder, liquid, emulsion, paste, cream, gel, mousse, ointment, sheet, etc.

The agents for cutaneous application of the present invention may include, but are not limited to, such forms as powders, lotions, emulsions, creams, jells, ointments, face masks, solid soaps, liquid soaps, shampoos, rinses, bath salts, etc.

The skin cosmetics of the present invention may include, but are not limited to, such forms as lotions, toilet waters, milk emulsions, beauty oils, beauty creams, beauty jells, face masks, powder foundations, liquid foundations, cream foundations, stick foundations, BB creams, beauty soaps, body soaps, face cleansers, cleansing lotions, cleansing milk emulsions, cleansing creams, cleansing oils, shampoos, rinses, treatments, hair tonics, hair growth formulas, bath salts, antiperspirants, etc.

Quasi-drugs are those products which have certain recognizable efficacy or effects, with mild actions on the human body. The quasi-drugs of the present invention include, but are not limited to, medicated cosmetics, medicated soaps, medicated shampoos, medicated rinses, medicated bath salts, medicated baby powders, medicated baby lotions, medicated hair growth formulas, etc.

The agents for cutaneous application, skin cosmetics, and quasi-drugs of the present invention contain as an active component one or more compounds in a class of rosacyanins, one or more compounds in a class of rosadelphins or combinations thereof that have a hyaluronidase inhibiting effect, a collagenase inhibiting effect, an elastase inhibiting effect, an MMP-1 production suppressing effect, and a collagen synthesis promoting effect, so they have a function for providing moisture to the skin and effectively preventing or ameliorating the drying of the skin, its wrinkling or sagging, roughened skin, or chapped skin. Hence, the skin cosmetics of the present invention are expected to prevent or ameliorate dry skin, sensitive skin, oily skin, or other skin conditions, thereby preventing or ameliorating the aging of the skin as evidenced by wrinkles, sags, or nasolabial folds.

The contents of the active components in the hyaluronidase inhibitors, collagenase inhibitors, elastase inhibitors, MMP-1 production suppressors, collagen synthesis promoters, agents for cutaneous application, skin cosmetics, and quasi-drugs of the present invention, namely, the compounds in a class of rosacyanins, the compounds in a class of rosadelphins, the extracts of plants of the family Rosaceae containing compounds in a class of rosacyanins, and the extracts of plants of the family Rosaceae containing compounds in a class of rosadelphins, may be determined in any desired way by considering the aspect of effects. For example, in the hyaluronidase inhibitors, collagenase inhibitors, elastase inhibitors, MMP-1 production suppressors, collagen synthesis promoters, agents for cutaneous application, or skin cosmetics, one or more components selected from the group consisting of the compounds in a class of rosacyanins, the compounds in a class of rosadelphins, the extracts of plants of the family Rosaceae containing compounds in a class of rosacyanins, and the extracts of plants of the family Rosaceae containing compounds in a class of rosadelphins are preferably contained, taken together, in amounts between 0.000001 to 99.9 wt %, more preferably between 0.00005 to 50 wt %, and even more preferably between 0.00001 to 10 wt %.

The present invention is described in greater detail by means of the following Examples which are in no way intended to limit the scope of the present invention. Persons skilled in the art may use the present invention as they are changed or modified in various ways, which are also included in the scope of the present invention.

EXAMPLE 1

(Isolation of Rosacyanins)

In accordance with the methods of JP 2002-201372 A, the following rosacyanins, i.e., rosacyanin A1, rosacyanin A2 and rosacyanin B, were obtained from petals of the rose variety "Madame Violet."

EXAMPLE 2

(Preparing an Extract from the Petals of a Plant of the Family Rosaceae Containing Rosadelphins)

Petals (110 g) of the rose variety APPLAUSE frozen at −80° C. were crushed into fragments in a polyvinyl bag with a wooden mallet as they were kept frozen. After adding 1.5 L of 70% ethanol, the fragments were subjected to extraction in an ultrasonic cleaner under sonication for 20 minutes. After the extraction step, filtration with suction was performed through No. 2 filter paper (Toyo Roshi Kaisha, Ltd.) with a Buchner funnel (12.5 cm$\phi$) and the filtrate was concentrated under reduced pressure with a rotary evaporator until its volume decreased to about a fifth of the original value, with ethanol being distilled off; the concentrate was then freeze-dried, producing a powder with a dry weight of 8.33 g (yield from raw petals: 7.57%)

EXAMPLE 3

(Purifying Rosadelphins-Containing Fractions and Compounds in a Class of Rosadelphins)

<Materials and Methods>

Petals (1100 g) of the rose variety APPLAUSE were freeze-crushed into fragments in liquid nitrogen with an EXCEL AUTO HOMOGENIZER and the fragments were added to a solution prepared by mixing 5.5 L of acetonitrile, 4.4 L of Milli-Q water and 55 ml of TFA to give 0.5% TFA-containing 50% acetonitrile (the solution weighing 11 L including the moisture of the petals), followed by immersion overnight. Filtration with suction was performed three times with a Buchner funnel (18 cm$\phi$) precoated with 50 g of Hyflo Super-Cel (diatomaceous earth) and the filtrate was continuously concentrated with a rotary evaporator until its volume was less than half of the original value.

The liquid concentrate was loaded on 2.2 L of adsorbent resin HP-20 (Mitsubishi Chemical Corporation) equilibrated with water. After washing with 2.2 L of water, the resin was left to stand overnight and after washing with additional 4.4 L of water (to give a total of 3 column volumes (CV)), elution was performed with 6.6 L of 0.1% TFA-containing 20% acetonitrile to give 13 fractions each weighing 500 ml. The first to fourth fractions (1-4 Fra.) did not contain any eluate, so they were discarded together with the washing solvent. The fifth to thirteenth fractions (5-13 Fra.) were concentrated under reduced pressure and freeze-dried. The blue pigments remaining in the column were eluted with 6.6 L of 0.1% TFA-containing 60% acetonitrile into nine fractions, followed by concentration under reduced pressure and freeze-drying. The seventh to ninth fractions (7-9 Fra.) were consolidated. A fraction containing a blue pigment (rosadelphin A1) eluted before and after the 60%-fraction 4.

The 60%-fraction 4 and the 60%-fraction 5 were purified by preparative HPLC under the following conditions. The column was Develosil-ODS-HG (product of Nomura Chemical Co., Ltd.: 5 cm$\phi$×50 cm); mobile phase A was 0.5% TFA/water and mobile phase B was 0.5% TFA/50% acetonitrile; the flow rate was 30 ml/min. Gradient elution was conducted as follows: B 30% (held for 30 min), linear gradient from B 30%→B 100% (over 50 min), and B 100% (held for 20 minutes). Detection was conducted at an absorbance of 260 nm ($A_{260}$). The blue pigment containing fractions eluting at 67-82 min were collected and freeze-dried. Chromatography was run six times for the 60%-4 Fra. and twice for the 60%-5 Fra.

The freeze-dried samples were loaded in five divided portions on a Sephadex LH-20 column (Pharmacia, 200 mL) equilibrated with 50% acetonitrile. With elution being conducted with 50% acetonitrile, fractions containing blue pigments were collected under visual inspection and freeze-dried.

The resulting freeze-dried products were subjected to another process of preparative HPLC in the following manner.

The column was YMC pack Polymer C18 (2 cm$\phi$×30 cm; YMC Co., Ltd.); mobile phase A was 0.5% TFA/water, and mobile phase B was 0.5% TFA/acetonitrile; at a flow rate of 6 ml/min, gradient elution was performed starting with B 32.5% (held for 30 min) through a linear gradient of B 32.5%→B 45% (over 50 min) and ending with B 45% (held for 30 min); detection was conducted with a PDA detector to gather data for 250-650 nm; chromatogram peaks at $A_{260}$ and $A_{560}$ were collected and the blue pigment eluting in the 80-94 min period was sampled as rosadelphin A1 and freeze-dried. Chromatography was run for a total of 5 times.

Component analyses were performed by HPLC-TOF-MS as follows.

<Conditions for HPLC Analysis>

Column: SHODEX ODP-40-2D (2 mm$\phi$×150 mm; Showa Denko K.K.)
Mobile phase A: 1% HCOOH/$H_2O$
Mobile phase B: 0.1% HCOOH/$CH_3CN$
Eluting conditions: B conc. 10%→60% (15 min), B conc. 60% iso (5 min)→10% (1 min), B conc. 10% (15 min)
Column temperature: 40° C.
Flow rate: 0.2 ml/min
Detection wavelength: PDA (250-600 nm), $A_{270}$ & $A_{560}$
Sample injection: 3 µL <Conditions for MS>

MS measurements were conducted with Q-TOF Premier (product of Micromass) in a positive V mode using ESI with a Z spray ion source. Mass calibration was performed by lock spray and leucine enkephalin (m/z 556.2771 $[M+H]^+$) was used as the reference. TOF-detector voltage: 2000 V; Capillary: 2.7 KV; Cone: 50 V; Source Temp: 150° C.; Desolvation Temp: 250° C.

Rosadelphins A1, B and A2 provided molecular ions that respectively had theoretical m/z values of 1221.1268 $[M]^+$, 435.0352 $[M]^+$, and 1373.1378 $[M]^+$ and their respective molecular formulas were $C_{56}H_{37}O_{32}$, $C_{22}H_{11}O_{10}$, and $C_{63}H_{41}O_{36}$. Purification was performed by making validation for rosadelphins based on the mass chromatograms for these molecular ions.

<Results>

(1) Fractions from HP-20 Column

The fractions from the HP-20 column were collectively freeze-dried as shown in Table 1.

TABLE 1

Yields of elution of HP-20 fractions with 60% acetonitrile

| | Before concentration (ml) | Weight (g) |
|---|---|---|
| Liquid concentrate filtration residue | | 3.94 |
| 60% MeCN-1,2 | 900 500 | 1.95 |

TABLE 1-continued

Yields of elution of HP-20 fractions with 60% acetonitrile

|  | Before concentration (ml) | Weight (g) |
|---|---|---|
| 60% MeCN-3 | 100 | 0.64 |
| 60% MeCN-4 | 300 | 11.39 |
| 60% MeCN-5 | 1,000 | 4.86 |
| 60% MeCN-6 | 1,000 | 0.11 |
| 60% MeCN-7,8,9 | 1000 1000 500 | 0.05 |

The eluates with 60% acetonitrile were chiefly composed of hydrolyzable tannins and blue pigments (delphinidin bound to tannins), with 60%-3 Fra, 4 Fra and 5 Fra each containing rosadeiphins A1 and A2.

(2) Results of Fractionation with 5 cmϕ ODS-HPLC

Preparative HPLC was performed in a sequence of five runs and the fractions containing rosadelphin A1 as well as the preceding and subsequent fractions were collected and freeze-dried. Loading of 11.27 g gave 2.49 g of pigment fractions (yield: 22.1%). The yield of the fractions containing rosadelphin A1 was 5.6%.

(3) Results of Fractionation with LH-20 Column

Fractionation with LH-20 involved separation of fractions by visual inspection. The samples were the freeze-dried powders obtained in (2) above using fractions from the ODS-HG column and loading was performed in a sequence of five times. After elution with 50% acetonitrile, elution with 80% acetone was effected and yet there was a permanently adsorbed purple-colored component, so the resin was taken out of the column and a pigment was eluted with 1N—HCl (0.2 ml)/EtOH (30 ml). The recovered dye was mainly composed of rosadelphin B.

Five runs of chromatography gave fractions containing rosadelphin A1 in purities of 20-70%.

(4) Results of Fractionation with 2 cmϕ Polymer C18 Column

A chromatogram for rosadelphin A1 as purified through the Polymer C18 column ($A_{560}$) is shown in FIG. 1.

(5) Results of Analysis by LC-MS

Fractionation of rosadelphins was carried out with each result of analysis being checked by LC-TOF-MS against the mass chromatogram for rosadelphin A1 (m/z 1221.14).

As a result of purification, rosadelphin A1 having a purity higher than 90% was obtained in an amount of 3.9 mg.

EXAMPLE 4

(Hyaluronidase Inhibition Test)
<Materials and Methods>

Tests for hyaluronidase inhibition of the extract prepared in Example 2 (hereinafter referred to as the "blue rose petal extract"), the HP-20 column fractions of the blue rose petal extract (60% acetonitrile fractions) and rosadelphin A1 were carried out in accordance with a modified version of the method described by Yumie Maeda et al. in *Shokukin Eiseigaku Zasshi* (Journal of the Food Hygiene Society of Japan) 31(3), 233-237 (1990). Hyaluronic acid is decomposed by hyaluronidase to give N-acetylhexosamine. To measure the hyaluronidase inhibitory activity, the reducing terminal N-acetylglucosamine was quantified in terms of absorbance due to color development as labeled by p-dimethylaminobenzaldehyde (product of Wako Pure Chemical Industries, Ltd. which is hereinafter abbreviated as p-DAB).

A sample solution (40 μL) in 10% DMSO was mixed with 20 μL of 1000 U/mL hyaluronidase (product of Sigma) dissolved in 0.1 M acetate buffer (pH 4.0) and the mixture was preheated at 37° C. for 20 minutes. To the heated mixture, 40 μL of 0.5 mg/mL Compound 48/80 (product of Sigma) dissolved in the same buffer was added and the resulting mixture was allowed to settle at 37° C. for 20 minutes undisturbed until the hyaluronidase was activated. To the solution, 100 μL of a solution of 0.8 mg/mL potassium hyaluronate was added to give a final concentration of 0.4 mg/mL and reaction was effected at 37° C. for 40 minutes; thereafter, 40 μL of 0.4 N sodium hydroxide in solution was added and the mixture was cooled with ice to quench the reaction. To the reaction mixture, 40 μL of 0.8 M boric acid in solution adjusted to pH 9.1 with 6 N NaOH was added and the resulting mixture was boiled at 100° C. for 3 minutes. The mixture was then cooled to room temperature in ice bath; to the cooled mixture, 1.2 mL of 10 mg/mL p-dimethylaminobenzaldehyde (p-DAB) in solution was added while it was shielded from light and after reaction was effected at 37° C. for 20 minutes, the absorbance at 585 nm ($A_{585}$) was measured. The hyaluronidase inhibitory activity of the sample was expressed in terms of percent inhibition calculated from the following formula:

$$\text{Percent inhibition (\%)} = \{1-(a-b)/(c-d)\} \times 100$$

a: $A_{585}$ of the sample solution to which the enzyme was added b: $A_{585}$ of the sample solution to which no enzyme was added c: $A_{585}$ of the control solution to which the enzyme was added d: $A_{585}$ of the control solution to which no enzyme was added.

A positive control was prepared by adding not the sample solution, but 800 μg/ml (1.56 mM as molar concentration) of sodium chromoglycate (product of Sigma which is hereinafter abbreviated as DSCG) in an amount of 40 μL to give a test concentration of 160 μg/ml.

<Results>

(1) Hyaluronidase Inhibitory Test with 60% Acetonitrile Fractions

The 60% acetonitrile fractions obtained by fractionating the blue rose petal extract on the HP-20 column were measured for the percent hyaluronidase inhibition (%) at test concentrations of 10 and 20 μg/ml to give the results shown in Table 2. TOF-MS analyses confirmed that the third to fifth fractions (3-5 Fra.) contained rosadelphin A1, a pigment characteristic of blue roses, with the contents in 4 Fra. and 5 Fra. being higher than that in 3 Fra.

At the test concentration which was one half the value for the blue rose petal extract, 3-6 Fra. showed stronger hyaluronidase activities than the blue rose petal extract and 4 Fra. having the highest content of rosadelphin A1 showed the strongest activity. These results suggested the possibility that 3-5 Fra. contained the active components, among which rosadelphin A1 was the active component in the blue rose petal extracts that displayed the hyaluronidase inhibitory activity.

TABLE 2

Percent hyaluronidase inhibition (%) by 60% acetonitrile fractions

| Sample name | Percent inhibition (%) | | |
|---|---|---|---|
|  | 10 μg/ml | 20 μg/ml | 40 μg/ml |
| Blue rose petal extract | — | — | 30.8 |

TABLE 2-continued

Percent hyaluronidase inhibition (%) by 60% acetonitrile fractions

| Sample name | Percent inhibition (%) | | |
|---|---|---|---|
| | 10 µg/ml | 20 µg/ml | 40 µg/ml |
| 60% acetonitrile-1,2 Fra. | 5.5 | 18.6 | — |
| 60% acetonitrile-3 Fra. | 16.7 | 36.7 | — |
| 60% acetonitrile-4 Fra. | 12.5 | 41.4 | — |
| 60% acetonitrile-5 Fra. | 12.7 | 36.0 | — |
| 60% acetonitrile-6 Fra. | 9.9 | 34.7 | — |
| 60% acetonitrile-7,8,9 Fra. | 5.5 | 19.8 | — |

* Percent inhibition by 160 µg/ml DSCG: 33.3%

(2) Hyaluronidase Inhibition Tests with Rosadelphin A1 and Analog Compounds Thereof The blue pigment component rosadelphin A1 purified from the blue rose petal extract was measured for the percent hyaluronidase inhibition (%) at test concentrations of 20, 40 and 80 µg/ml to give the results shown in Table 3. Clearly, rosadelphin A1 was the active component in the blue rose petal extract. Since rosadelphin A1 showed strong activity in a concentration dependent manner, its dose response quality was also confirmed.

In addition, tellimagrandin 1 as a structural constituent of rosadelphin A1 and rosacyanin A1 as the blue pigment component in the host strain were both measured for activity and the intensities of their activities were compared. Rosacyanin A1 showed comparable activity to rosadelphin A1. Tellimagrandin 1, a hydrolyzable tannin contained in APPLAUSE and also found in plants of the family Rosaceae, was also active, though not so active as rosadelphin A1.

One of the commercial extracted ingredients of rose petals is ROSE CRYSTA-70 (trademark) manufactured by Toyo Hakko Co. Ltd. This ingredient is a material that contains eugeniin as a hydrolyzable tannin and which must satisfy the requirement that it have a total phenol content of 70%. The blue rose petal extract showed a stronger hyaluronidase inhibitory activity than ROSE CRYSTA-70 (trademark) (Table 4); thus, data were obtained supporting that the group of blue pigments including rosadelphin A1 have stronger activity than hydrolyzable tannins.

As it turned out, the hyaluronidase inhibitory activity of the respective compounds decreased in the following order: (rosacyanin A1, rosadelphin A1)>blue rose petal extract>tellimagrandin 1. Since rosadelphin A1 was found to have stronger activity than tellimagrandin 1, it is believed to have a superior effect for providing a moisturizing action than the conventionally used rose extract as an ingredient.

[Table 3]

TABLE 3

Percent hyaluronidase inhibition (%) by rosadelphin A1 and analog compounds thereof

| Sample name | Percent inhibition (%) | | | IC50 (µg/ml) | Titer (1/IC$_{50}$) |
|---|---|---|---|---|---|
| | 20 µg/ml | 40 µg/ml | 80 µg/ml | | |
| Blue rose petal extract | 14.7 | 29.9 | 63.2 | 64.1 | 15.6 |
| Rosadelphin A1 | 24.4 | 48.2 | 95.3 | 41.5 | 24.1 |
| Rosacyanin A1 | 24.7 | 49.1 | 93.2 | 40.8 | 24.5 |
| Tellimagrandin 1 | — | — | 64.8 | 196.5 | 5.1 |

* Percent inhibition by 160 µg/ml DSCG: 22.3%

[Table 4]

TABLE 4

Percent hyaluronidase inhibition (%) by the blue rose petal extract and ROSE CRYSTA-70 (trademark)

| Sample name | Percent inhibition (%) 30 µg/ml | Total phenol content (%)** |
|---|---|---|
| Blue rose petal extract | 71.0 | 43.6 |
| ROSE CRYSTA-70 | 41.0 | 74.1 |

* Percent inhibition by 160 µg/ml DSCG: 33.7%
**Total phenol content was calculated in terms of gallic acid by the Folin-Ciocalteu method.

Thus, it became clear that the blue rose petal extract, in particular, a fraction containing the blue pigment rosadelphins; rosadelphin A1; and rosacyanin A1 as a non-recombinant blue pigment, had strong hyaluronidase inhibitory activity.

EXAMPLE 5

(Collagenase Inhibition Test)
<Materials and Methods>

The blue rose petal extract, fractions thereof as products of treatment on a column (60% acetonitrile fractions), rosadelphin A1, rosacyanin A1, and tellimagrandin 1 were subjected to a collagenase inhibition test in accordance with a modified version of the method described in a document (Wunsch et al., Hoppe Seylers Z Physiol Chem., 333, 149-51 (1963)). For details, see below.

An enzyme solution was prepared by dissolving 10 mg of collagenase Type IV (product of Sigma) in 1 mL of dissolved water to give a concentration of 100 µg/mL (55.1 units/mL) and diluted 50 folds just before use. A substrate solution was prepared by dissolving PZ-peptide (4-phenylazo-benzyloxycarbonyl-Pro-Leu-Gly-Pro-D-Arg-OH) (Pz-Pro-Leu-Gly-Pro-D-Arg-OH; product of Sigma) in a 20 nmol/L calcium chloride containing tris-HCl buffer (pH 7.1) to give a concentration of 0.5 µg/mL. To 20 µL of a solution of sample dissolved in 10% DMSO, 20 µL of the enzyme solution and 160 µL of the substrate solution were added and the mixture was subjected to reaction at 37° C. for 30 minutes. Subsequently, 400 µL of a 25 mM citric acid solution was added to quench the reaction and Pz-Pro-Leu in the reaction mixture was extracted with 2 mL of ethyl acetate. The resulting ethyl acetate layer was measured for absorbance at a wavelength of 320 nm, with ethyl acetate being used as a control. The inhibitory activity of each sample was calculated in terms of the percent inhibition determined by the following formula:

Percent collagenase inhibition (%)=$\{1-(a-b)/(c-d)\} \times 100$ a: Absorbance after 30 mM reaction in the presence of added sample b: Absorbance after 0 mM reaction in the presence of added sample c: Absorbance after 30 min reaction in the absence of added sample d: Absorbance after 0 min reaction in the absence of added sample.

When the collagenase activity is completely inhibited, the percent collagenase inhibition (%) determined by the above formula is 100%. Compounds showing high values of "percent inhibition (%)" may well be described as being more active as inhibitor.

In the collagenase inhibition test, a positive control was prepared by adding not the sample solution, but 800 μg/mL (0.176 mM as molar concentration) of isoamylphosphonyl-Glycyl-L-Prolyl-L-Alanine, dipotassium salt; $C_{15}H_{26}K_2N_3O_6P$ (product of Elastin Products Company, Inc., which is hereinafter abbreviated as IP304) in an amount of 20 μL (or 80 μg/mL as concentration during reaction).

<Results>

(1) Collagenase Inhibition Test with 60% Acetonitrile Fractions

The 60% acetonitrile fractions obtained by fractionating the blue rose petal extract on the HP-20 column were measured for the percent collagenase inhibition (%) at test concentrations of 40 and 80 μg/ml to give the results shown in Table 5. TOF-MS analyses confirmed that the third to fifth fractions (3-5 Fra.) contained the pigment component rosadelphin A1 which was characteristic of roses having the flavonoid 3',5'-hydrolase gene, with the contents in 4 Fra. and 5 Fra. being higher than that in 3 Fra.

At the test concentration which was one half the value for the blue rose petal extract, 3-6 Fra. showed stronger collagenase inhibiting activities than the blue rose petal extract, and so did 1, 2 and 6 Fra. at the same test concentration as the blue rose petal extract. These results suggested that 3-5 Fra. contained the active components and that rosadelphin A1 was the active component in the blue rose petal extract that displayed the collagenase inhibitory activity. In addition, not only 3-5 Fra. which contained rosadelphin A1 but all other 60% acetonitrile fractions also possessed comparatively high levels of activity, thus making it clear that the group of blue pigment compounds generally were active.

TABLE 5

Percent collagenase inhibition (%) by 60% acetonitrile fractions

| Sample name | Percent inhibition(%) | |
|---|---|---|
| | 40 μg/mL | 80 μg/mL |
| Blue rose petal extract | — | 44.7 |
| 60% acetonitrile-1,2 Fra. | 42.7 | 60.3 |
| 60% acetonitrile-3 Fra. | 50.3 | 60.6 |
| 60% acetonitrile-4 Fra. | 48.7 | 59.2 |
| 60% acetonitrile-5 Fra. | 49.4 | 62.1 |
| 60% acetonitrile-6 Fra. | 40.5 | 52.0 |
| 60% acetonitrile-7,8,9 Fra. | 38.8 | 41.8 |

* Percent inhibition by 80 μg/mL IP304: 84.1%

(2) Collagenase Inhibition Tests with Rosadelphin A1 and Analog Compounds Thereof The blue pigment component rosadelphin A1 purified from the blue rose petal extract was measured for the percent collagenase inhibition (%) at a test concentration of 40 μg/ml to give the results shown in Table 6. Clearly, rosadelphin A1 was the active component in the blue rose petal extract.

In addition, tellimagrandin 1 as a structural constituent of rosadelphin A1 and rosacyanin A1 as the blue pigment component in the host strain were both measured for activity and the intensities of their activities were compared.

As regards the collagenase inhibitory activities of the respective compounds at 40 μg/mL, rosacyanin A1, tellimagrandin 1, and rosadelphin A1 each had a greater activity than the blue rose petal extract.

TABLE 6

Percent collagenase inhibition (%) by rosadelphin A1 and analog compounds thereof

| Sample name | Percent inhibition (%)* |
|---|---|
| Blue rose petal extract | 23.0 |
| Rosadelphin A1 | 42.3 |
| Rosacyanin A1 | 52.0 |
| Tellimagrandin 1 | 42.7 |

*Test concentration of each sample: 40 μg/ml
*Percent inhibition by 40 μg/ml IP304: 69.7%

EXAMPLE 6

(Elastase Inhibition Test)
<Materials and Methods>

The blue rose petal extract, fractions thereof as products of treatment on a column (60% acetonitrile fractions), rosadelphin A1, rosacyanin A1, and tellimagrandin 1 were subjected to an elastase inhibition test that was performed by the following method.

An enzyme solution was prepared by dissolving 0.1 ml of elastase (product of Sigma) in 0.2 M Tris buffer at pH 8.0 (hereinafter referred to as a Tris buffer) to give a concentration of 0.05 units/mL and diluted 100 folds just before use. A substrate solution was prepared by dissolving N-Succinyl-Ala-Ala-Ala-p-nitroanilide (product of Sigma) in a Tris buffer to give a concentration of 4 mM. To a 96-well plate, 50 μL of a solution of each sample dissolved in 10% DMSO and 50 μL of the enzyme solution were added and after mixing them with a plate shaker, the resulting mixture was preheated at 25° C. for 10 minutes. Subsequently, 100 μL of the substrate solution was added and after mixing with a plate shaker, reaction was carried out at 25° C. for 30 minutes and immediately thereafter, the liberation of p-nitroaniline was assayed by measuring the absorbance at a wavelength of 405 nm (hereinafter designated as $A_{405}$). $A_{405}$ measurement was also performed for a blank of sample solution that was prepared by adding a Tris buffer in place of the substrate solution, as well as for a control solution that was prepared by adding 10% DMSO in place of the sample solution. The inhibitory activity of each sample was calculated in terms of the percent inhibition determined by the following formula:

Percent elastase inhibition (%)=[(f−e)−{(b−a)−(d−c)}]/(f−e)×100 a: $A_{405}$(0 min) of the sample solution for enzymatic reaction b: $A_{405}$(30 min) of the sample solution for enzymatic reaction c: $A_{405}$(0 min) of the blank of sample solution
d: $A_{405}$(30 min) of the blank of sample solution
e: $A_{405}$(0 min) of the control solution
f: $A_{405}$(30 min) of the control solution.

When the elastase activity is completely inhibited, the percent elastase inhibition (%) determined by the above formula is 100%. Compounds showing high values of "percent inhibition (%)" may well be described as being more active as inhibitor.

In the elastase inhibition test, a positive control was prepared by adding not the sample solution, but 320 µg/mL (1.84 mM as molar concentration) of phenylmethanesulfonyl fluoride; $C_7H_7FO_2S$ (product of Sigma, which is hereinafter abbreviated as PMSF) in an amount of 50 µL (or 80 µg/mL as concentration during reaction).

<Results>

(1) Elastase Inhibition Test with 60% Acetonitrile Fractions

The 60% acetonitrile fractions obtained by fractionating the blue rose petal extract on the HP-20 column were measured for the percent elastase inhibition (%) at test concentrations of 40, 80 and 160 µg/ml to give the results shown in Table 7. TOF-MS analyses confirmed that the third to fifth fractions (3-5 Fra.) contained the pigment component rosadelphin A1 which was characteristic of blue roses, with the contents in 4 Fra. and 5 Fra. being higher than that in 3 Fra.

Among the tested 60% acetonitrile fractions, 4-9 Fra. showed stronger activities than the blue rose petal extract which was yet to be fractionated on the HP-20 column. Since 6-9 Fra. had particularly strong activity, it was clear that not only rosadelphins but also the group of blue pigment compounds generally had strong activity.

TABLE 7

Percent elastase inhibition (%) by 60% acetonitrile fractions

| Sample name | Percent inhibition (%) | | | | |
|---|---|---|---|---|---|
| | 40 µg/mL | 80 µg/mL | 160 µg/mL | 320 µg/mL | 640 µg/mL |
| Blue rose petal extract | — | — | 19.8 | 41.0 | 63.1 |
| 60% acetonitrile-1,2 Fra. | 13.8 | 7.4 | 5.4 | — | — |
| 60% acetonitrile-3 Fra. | 17.6 | 18.3 | 10.8 | — | — |
| 60% acetonitrile-4 Fra. | 24.2 | 24.5 | 29.8 | — | — |
| 60% acetonitrile-5 Fra. | 12.9 | 18.8 | 22.9 | — | — |
| 60% acetonitrile-6 Fra. | 31.6 | 48.7 | 62.5 | — | — |
| 60% acetonitrile-7,8,9 Fra. | 17.5 | 30.2 | 52.4 | — | — |

* Percent inhibition by 80 µg/mL PMSF: 94.1%

(2) Elastase Inhibition Tests with Rosadelphin A1

The blue pigment component rosadelphin A1 purified from the blue rose petal extract was measured for the percent elastase inhibition (%) at test concentrations of 40, 80 and 160 µg/ml to give the results shown in Table 8. Since rosadelphin A1 showed strong activity in a concentration dependent manner, its dose response quality was also confirmed.

In addition, tellimagrandin 1 as a structural constituent of rosadelphin A1 and rosacyanin A1 as the blue pigment component in the host strain were both measured for activity and the intensities of their activities were compared. Rosadelphin A1 showed comparable or more than comparable activity to rosacyanin A1. Tellimagrandin 1, a hydrolyzable tannin contained in plants of the family Rosaceae, showed weak activity whereas rosadelphin A1 and rosacyanin A1 showed strong activity; hence, it is assumed that by containing the group of blue pigment compounds, extracts derived from blue-hued rose petals have stronger activity than commercial rose extracts (essences).

TABLE 8

Percent elastase inhibition (%) by rosadelphin A1 and analog compounds thereof

| Sample name | Percent inhibition (%) | | | | |
|---|---|---|---|---|---|
| | 40 µg/mL | 80 µg/mL | 160 µg/mL | 320 µg/mL | 640 µg/mL |
| Blue rose petal extract | — | — | 12.4 | 21.1 | 58.0 |
| Rosadelphin A1 | 50.7 | 58.1 | 62.0 | — | — |
| Rosadelphin A1 | 31.8 | 40.4 | 49.4 | — | — |
| Tellimagrandin 1 | 5.9 | 4.6 | 6.5 | — | — |

* Percent inhibition by 80 µg/mL PMSF: 79.5%

EXAMPLE 7

(Collagen Synthesis Promotion Test)
<Materials and Methods>

Using a 0.5% fetal bovine serum containing Dulbecco's Modified MEM (0.5% FBS-DMEM), normal human fibroblasts were seeded on a 96-well plate at a cell density of $2.0 \times 10^4$ cells/well. Twenty-four hours after seeding, the 0.5% FBS-DMEM was exchanged with a 0.5% FBS-DMEM containing a blue rose petal extract that was obtained by a sequence of dilutions with the blue rose petal extract starting from a maximum concentration at which the extract had no cytotoxicity. The positive control was 25 µM ascorbic acid phosphate magnesium salt (VC—PMg). Culture was continued for 24 hours in a medium containing products of column treatment of the blue rose petal extract and, thereafter, the supernatant of the culture was recovered and subjected to ELISA. The cells were dissolved in a 0.5% Triton X-100 solution and their protein content was quantified by the BCA method.

A medium and a solution of collagen type I for constructing a calibration curve were placed on a highly adsorbent ELISA plate and after coating at 4° C. for 24 hours, a 1% bovine serum albumin (BSA) solution was used to perform blocking at 37° C. for an hour. For the primary antibody reaction, Anti-Human Collagen Type I antibody (Rabbit) was diluted with a 0.3% BSA solution and then added to carry out reaction at 37° C. for 1.5 hours. For the secondary antibody reaction, Histofine MAX-PO(R) (Rabbit) was diluted with a phosphate buffer and then added to carry out reaction at 37° C. for 1.5 hours.

Subsequently, a phosphate-citrate buffer (0.1 M, pH 4.0) containing 0.3 mg/mL 2,2'-azino-bis(3-ethylbenzothiazoline-6-sulfonic acid) diammonium salt (ABTS) and 0.03% hydrogen peroxide was added and after 30-min reaction, the absorbance at 405 nm was measured with a microplate reader.

The amount of collagen type I in the medium was calculated from the calibration curve constructed by measurement on the same ELISA plate. The calculated amount of collagen type I in the medium was divided by the protein content of the whole cells to determine the amount of synthesized collagen type I per unit protein content. The respective amounts of synthesized collagen type I were checked for significant differences by Student's t-test and compared with the result from the control.

<Results>

Figure 2:
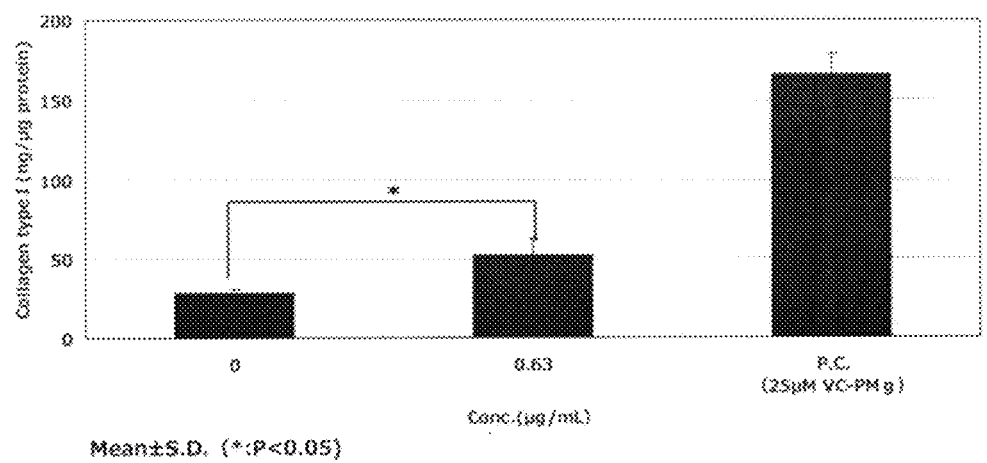
FIG. 2 shows a quantitative comparison for the synthesis of collagen type I.

The amount of collagen type I synthesized by the blue rose petal extract is shown in FIG. 2. Collagen type I was found to be synthesized in a significantly increased amount upon addition of the test sample.

EXAMPLE 8

(MMP-1 Production Suppression Test)

MMP-1 (matrix metalloproteinase 1) also known as an interstitial collagenase is a metalloproteinase (a proteinase having a metal ion coordinated in the active center) which is involved in the decomposition of collagen. By inhibiting the production of MMP-1, the decomposition of collagen is suppressed.

The blue rose petal extract was investigated for its effect on the suppression of MMP-1 production. Neonatally derived normal human dermal fibroblasts ((NHDF-NB purchased from Kurabo Industries Ltd.) were used as dermal fibroblast cells and the investigation was made with reference to the production volume of MMP-1 as an index.

The dermal fibroblast cells were seeded on a 24-well plate and incubated at 37° C. and a $CO_2$ concentration of 5 vol % until they became confluent. Thereafter, the blue rose petal extract dissolved in DMSO was added at concentrations of 0, 5, 10 and 20 mg/mL. DMSO was added to give a final concentration of 0.1%. After 24-hr culture, IL-1β was added to the medium to give a final concentration of 100 μg/mL. Some of the wells to which only a DMSO solution was added were used as a control having no IL-1β added thereto. After 48-hr culture, the supernatant of the culture was recovered and the proMMP-1 secreted into the medium was quantified as the production volume of MMP-1. Quantification of proMMP-1 was performed using a quantitative ELISA Kit (product of R&D Systems) in accordance with the attached manual. The results of quantification were shown in relative values (%), with the production volume of MMP-1 from the control being taken as 100% (Table 9).

TABLE 9

| | Addition concentration of the blue rose petal extract (μg/mL) | Addition concentration of IL-1β (μg/mL) | MMP-1 Production volume (relative value) |
|---|---|---|---|
| Control | 0 | 0 | 100 ± 12.2 |
| Blue rose petal extract | 0 | 100 | 403.2 ± 5.8 |
| | 5 | 100 | 114.6 ± 4.9 |
| | 10 | 100 | 110.1 ± 5.5 |
| | 20 | 100 | 85.7 ± 11.6 |

When the dermal fibroblast cells had only IL-1β added thereto, the volume of MMP-1 they produced was about four times as great as the value for the control. However, when the cells were treated with the blue rose petal extract, the production of MMP-1 due to IL-1μ was markedly suppressed at all concentrations of the extract's addition.

These results showed that the blue rose petal extract has a superior MMP-1 production suppressing effect.

INDUSTRIAL APPLICABILITY

By containing the compounds in a class of rosacyanins or the compounds in a class of rosadelphins as an active component, the hyaluronidase inhibitors, collagenase inhibitors and elastase inhibitors of the present invention exhibit superior effects in preventing or ameliorating the drying, wrinkling or sagging of the skin and, hence, are useful for the development and manufacture of moisturizing and anti-aging agents for cutaneous application, skin cosmetics, and quasi-drugs.

The invention claimed is:

1. A method of inhibiting hyaluronidase, comprising administering an effective amount of, as an active component, one or more compounds selected from the group consisting of a compound in a class of rosacyanins as represented by the following general formula (I):

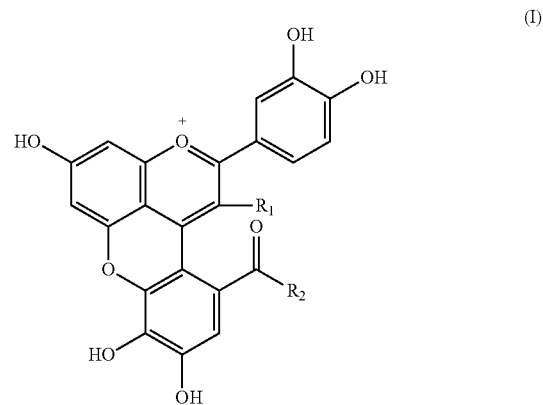

(I)

[where $R_1$ and $R_2$, taken together, form —O—; or alternatively, $R_1$ is the following group (a):

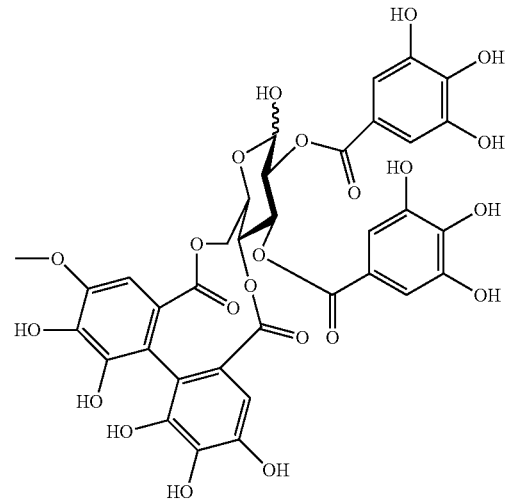

{provided that in group (a), the coordination (wavy line) to the hydroxyl group at position 1 of glucose indicates tautomerism of α- and β-forms} or the following group (b):

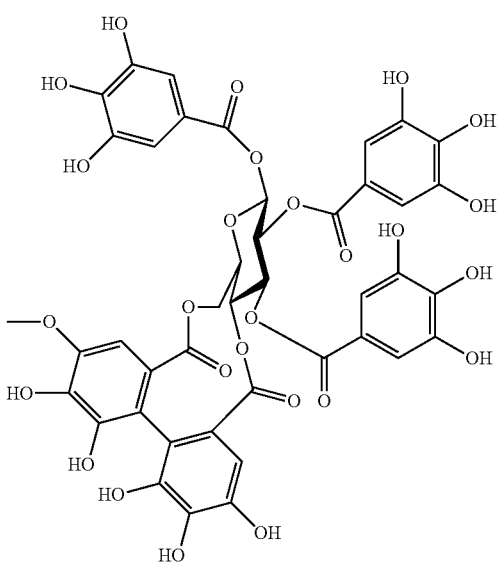

and R$_2$ is OH]; and a compound in a class of rosadelphins as represented by the following general formula (II):

(II)

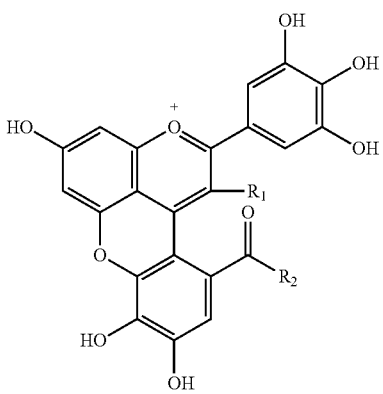

{where R$_1$ is the following formula (a):

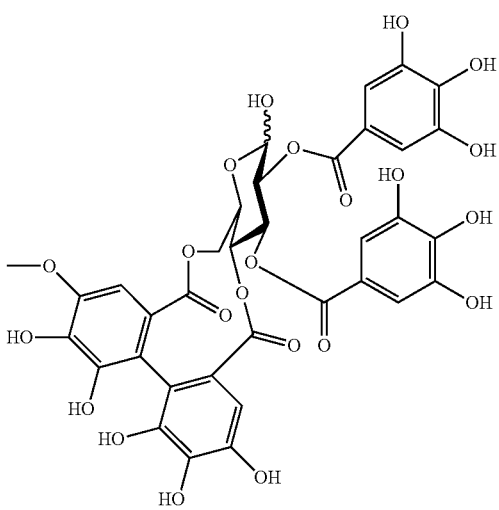

{provided that in group (a), the coordination (wavy line) to the hydroxyl group at position 1 of glucose indicates tautomerism of α- and β-forms} and R$_2$ is OH; or R$_1$ and R$_2$, taken together, form —O—; or R$_1$ is the following group (b):

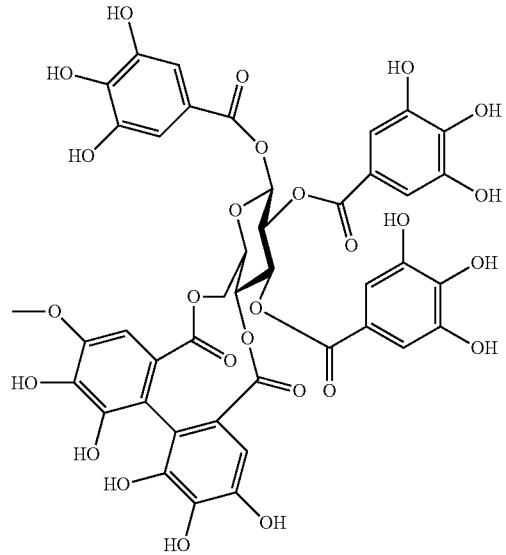

and R$_2$ is —OH}, to a subject in need thereof.

2. The method according to claim 1, wherein the compound in the class of rosacyanins is one or more compounds selected from the group consisting of rosacyanin A1 represented by the following formula:

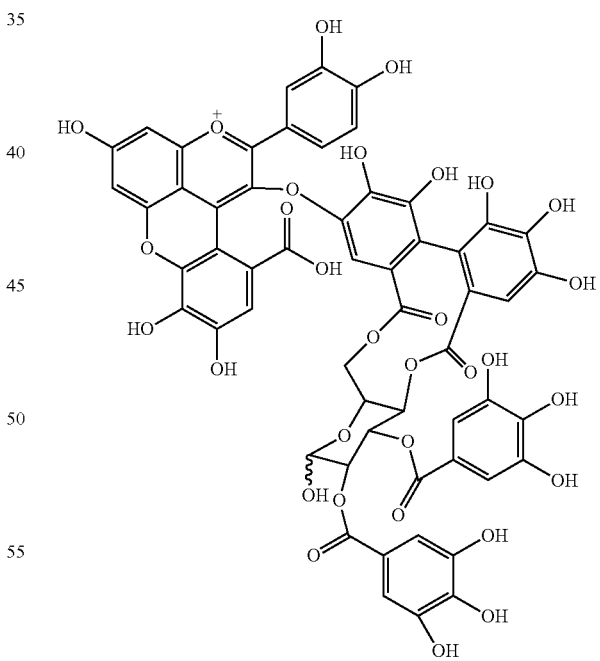

{provided that in this group, the coordination (wavy line) to the hydroxyl group at position 1 of glucose indicates tautomerism of α- and β-forms}, rosacyanin A2 represented by the following formula:

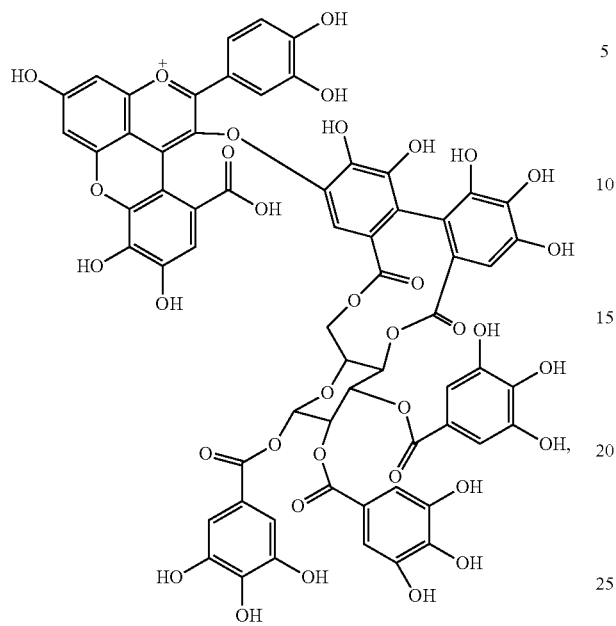

and rosacyanin B represented by the following formula:

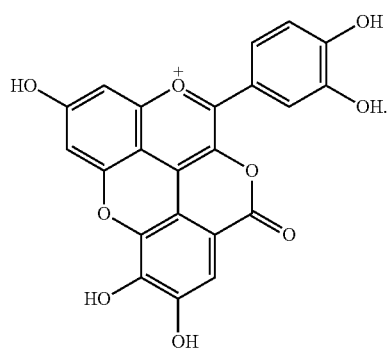

3. The method according to claim 1, wherein the compound in the class of rosacyanins is administered as an extract of a plant of the family Rosaceae that contains the compound in the class of rosacyanins.

4. The method according to claim 3, wherein the plant of the family Rosaceae that contains the compound in the class of rosacyanins is one or more plants of the family Rosaceae as selected from the group consisting of Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver.

5. The method according to claim 1, wherein the compound in the class of rosadelphins is one or more compounds selected from the group consisting of rosadelphin A1 represented by the following formula:

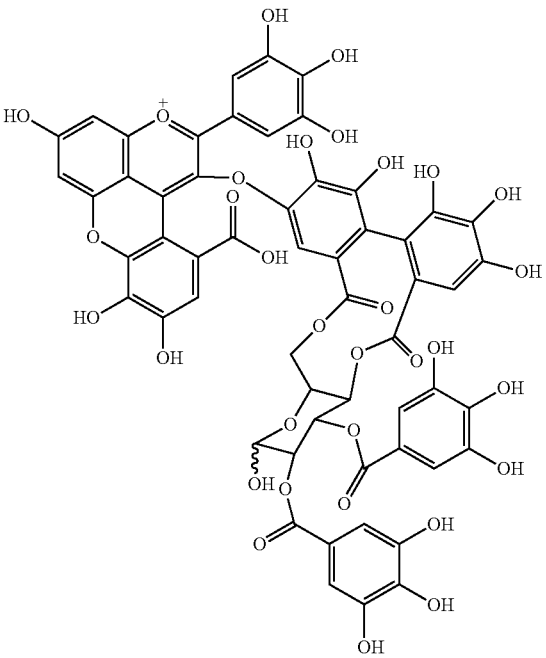

{provided that in this group, the coordination (wavy line) to the hydroxyl group at position 1 of glucose indicates tautomerism of α- and β-forms}, rosadelphin A2 represented by the following formula:

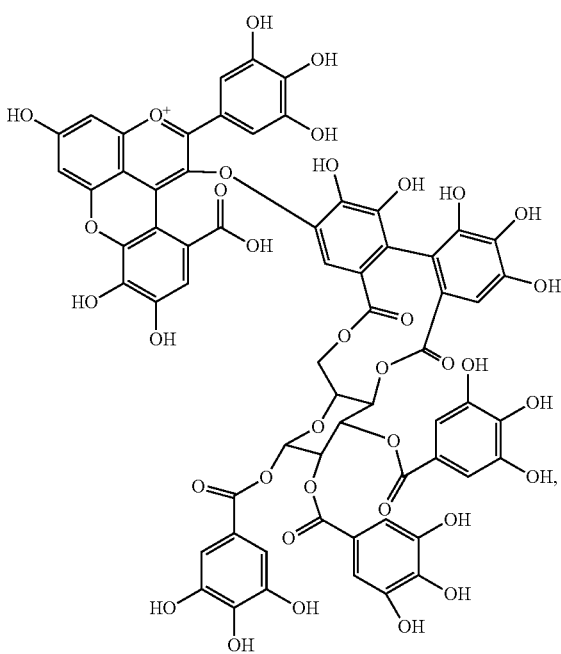 [SMILES: O=C(OC1OC2COC(=O)c3cc(Oc4c(-c5cc(O)c(O)c(O)c5)[o+]c5cc(O)cc6c5c4-c4c(C(=O)O)cc(O)c(O)c4O6)c(O)c(O)c3-c3c(cc(O)c(O)c3O)C(=O)OC2C(OC(=O)c2cc(O)c(O)c(O)c2)C1OC(=O)c1cc(O)c(O)c(O)c1)c1cc(O)c(O)c(O)c1]

and rosadelphin B represented by the following formula:

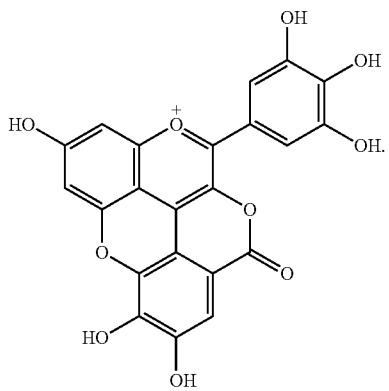

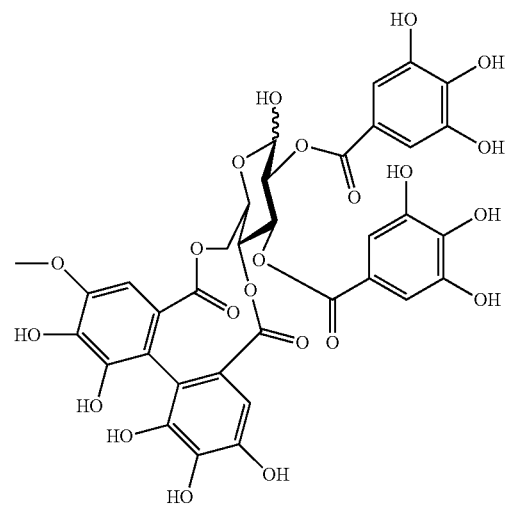

6. The method according to claim 1, wherein the compound in the class of rosadelphins is administered as an extract of a plant of the family Rosaceae that contains the compound in the class of rosadelphins.

7. The method according to claim 6, wherein the plant of the family Rosaceae that contains the compound in the class of rosadelphins is a plant of the family Rosaceae that contains the flavonoid 3', 5'-hydroxylase gene.

8. The method according to claim 1, wherein administration of said one or more compounds suppresses matrix metalloproteinase 1 (MMP-1) production.

9. The method according to claim 1, wherein administration of said one or more compounds promotes collagen synthesis.

10. The method according to claim 1, wherein administration of said one or more compounds is cutaneous administration.

11. A method of inhibiting collagenase, comprising administering an effective amount of, as an active component, one or more compounds selected from the group consisting of a compound in a class of rosacyanins as represented by the following general formula (I):

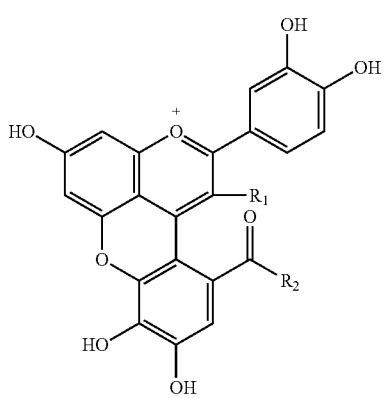

(I)

[where $R_1$ and $R_2$, taken together, form —O—; or alternatively, $R_1$ is the following group (a):

{provided that in group (a), the coordination (wavy line) to the hydroxyl group at position 1 of glucose indicates tautomerism of α- and β-forms} or the following group (b):

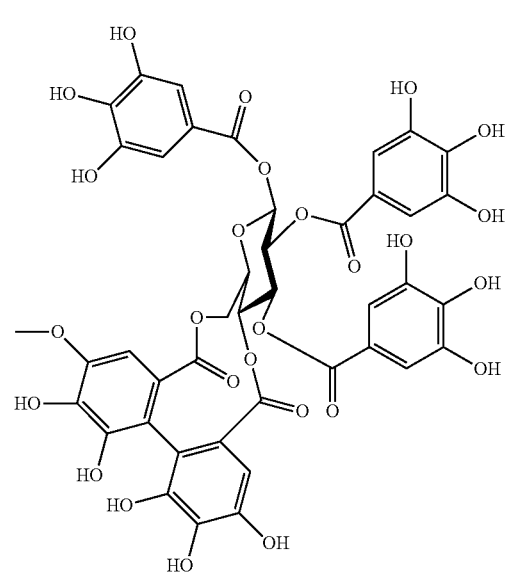

and $R_2$ is —OH]; and
a compound in a class of rosadelphins as represented by the following general formula (II):

(II)

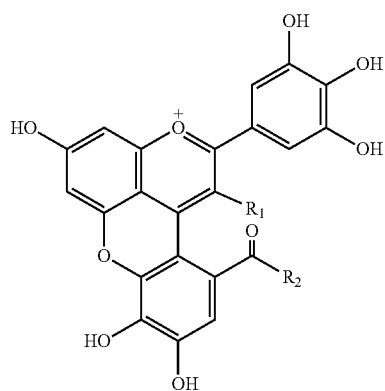

{where R₁ is the following formula (a):

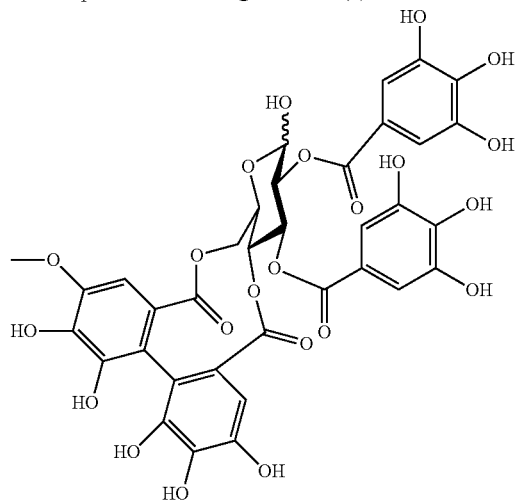

{provided that in group (a), the coordination (wavy line) to the hydroxyl group at position 1 of glucose indicates tautomerism of α- and β-forms} and R₂ is —OH; or R₁ and R₂, taken together, form —O—; or R₁ is the following group (b):

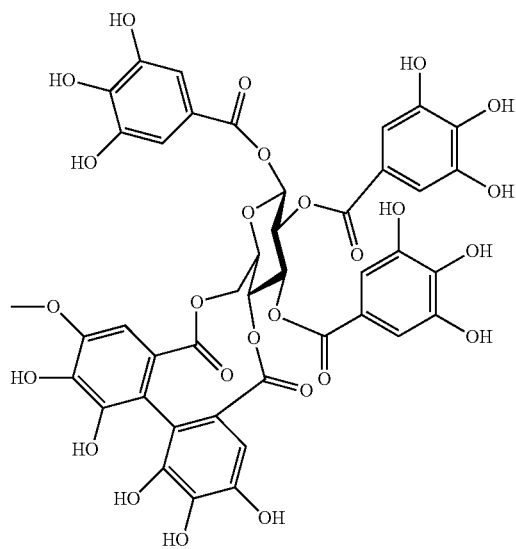

and R₂ is —OH}, to a subject in need thereof.

12. The method according to claim 11, wherein the compound in the class of rosacyanins is one or more compounds selected from the group consisting of rosacyanin A1 represented by the following formula:

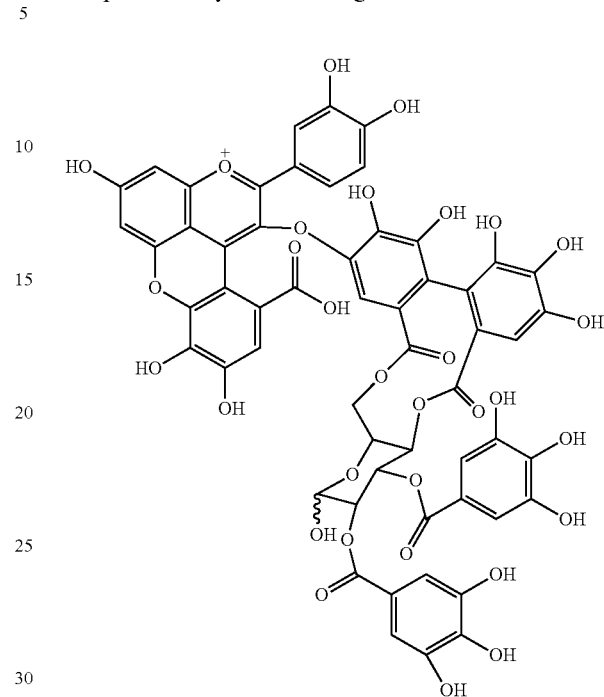

{provided that in this group, the coordination (wavy line) to the hydroxyl group at position 1 of glucose indicates tautomerism of α- and β-forms}, rosacyanin A2 represented by the following formula:

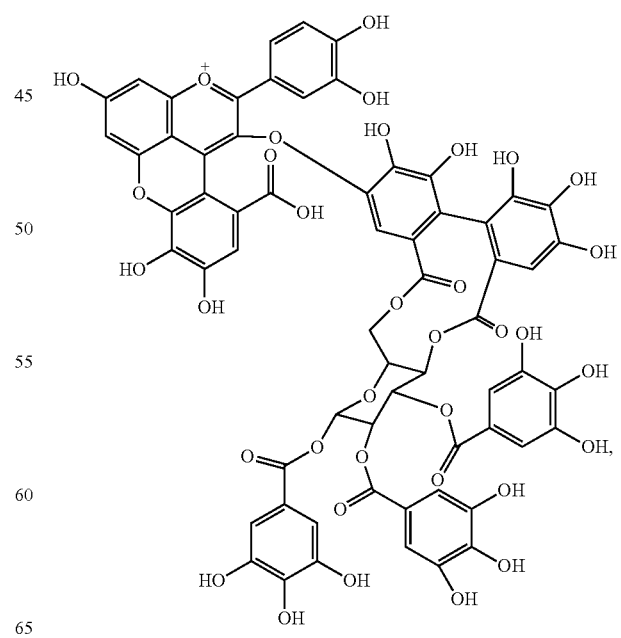

and rosacyanin B represented by the following formula:

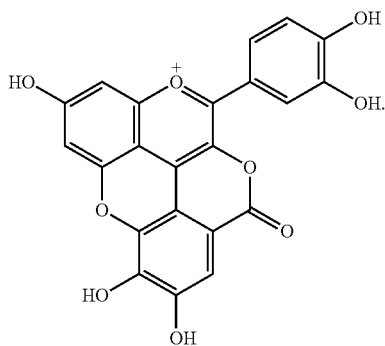

13. The method according to claim 11, wherein the compound in the class of rosacyanins is administered as an extract of a plant of the family Rosaceae that contains the compound in the class of rosacyanins.

14. The method according to claim 13, wherein the plant of the family Rosaceae that contains the compound in the class of rosacyanins is one or more plants of the family Rosaceae as selected from the group consisting of Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver.

15. The method according to claim 11, wherein the compound in the class of rosadelphins is one or more compounds selected from the group consisting of rosadelphin A1 represented by the following formula:

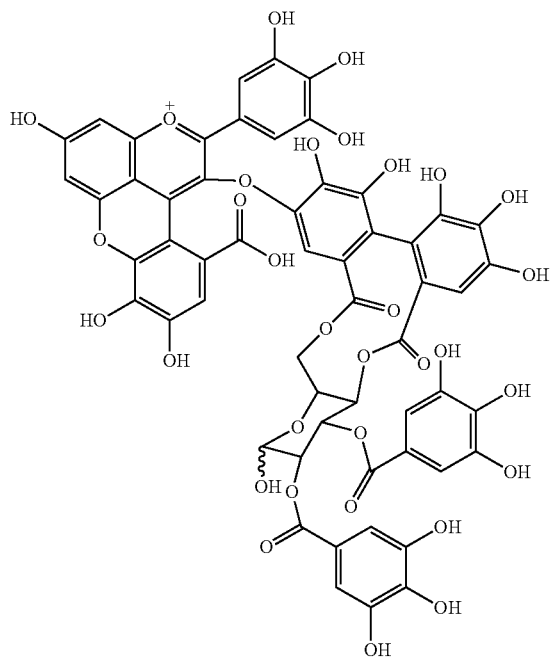

{provided that in this group, the coordination (wavy line) to the hydroxyl group at position 1 of glucose indicates tautomerism of α- and β-forms}, rosadelphin A2 represented by the following formula:

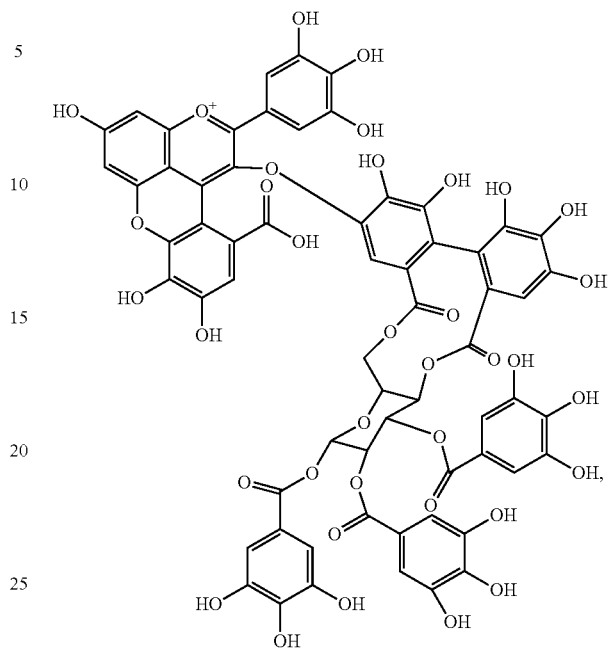

and rosadelphin B represented by the following formula:

16. The method according to claim 11, wherein the compound in the class of rosadelphins is administered as an extract of a plant of the family Rosaceae that contains the compound in the class of rosadelphins.

17. The method according to claim 16, wherein the plant of the family Rosaceae that contains the compound in the class of rosadelphins is a plant of the family Rosaceae that contains the flavonoid 3', 5'-hydroxylase gene.

18. The method according to claim 11, wherein administration of said one or more compounds suppresses matrix metalloproteinase 1 (MMP-1) production.

19. The method according to claim 11, wherein administration of said one or more compounds promotes collagen synthesis.

20. The method according to claim 11, wherein administration of said one or more compounds is cutaneous administration.

21. A method of inhibiting elastase, comprising administering an effective amount of, as an active component, one or more compounds selected from the group consisting of a compound in a class of rosacyanins as represented by the following general formula (I):

(I)

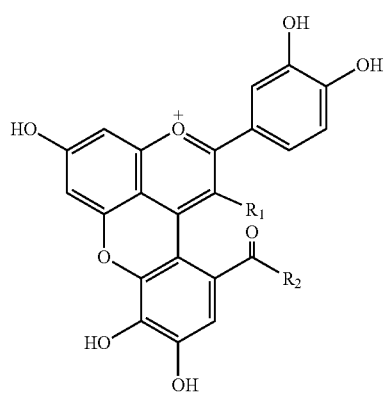

[where $R_1$ and $R_2$, taken together, form —O—; or alternatively, $R_1$ is the following group (a):

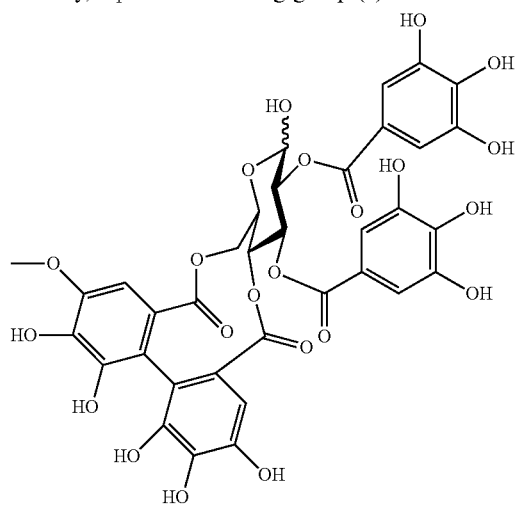

{provided that in group (a), the coordination (wavy line) to the hydroxyl group at position 1 of glucose indicates tautomerism of α- and β-forms} or the following group (b):

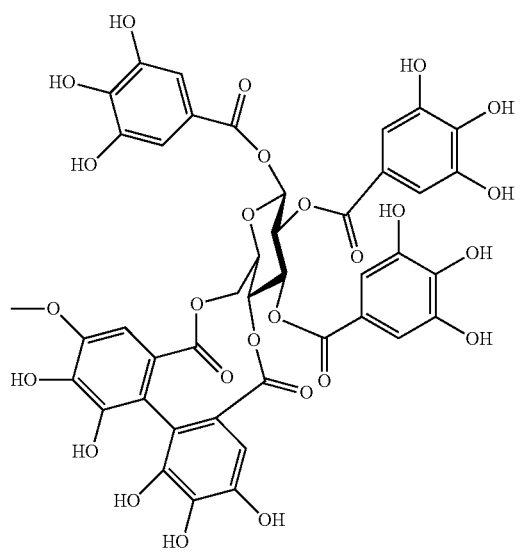

and $R_2$ is —OH]; and a compound in a class of rosadelphins as represented by the following general formula (II):

(II)

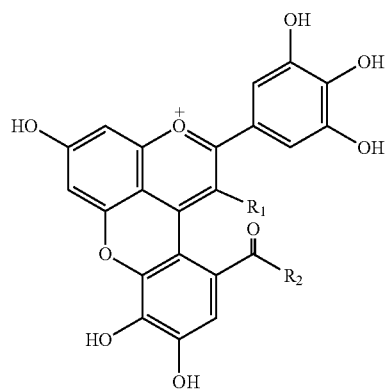

{where $R_1$ is the following formula (a):

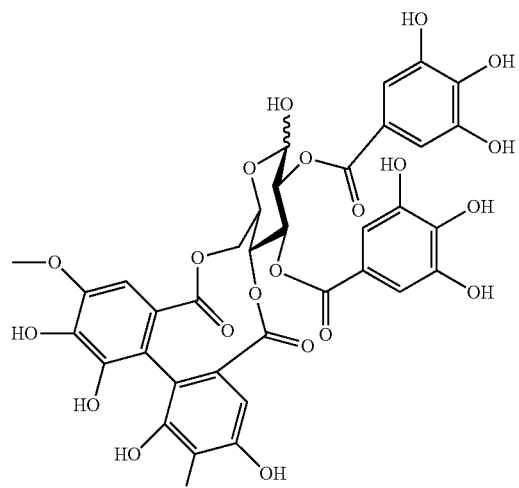

{provided that in group (a), the coordination (wavy line) to the hydroxyl group at position 1 of glucose indicates tautomerism of α- and β-forms} and $R_2$ is —OH; or $R_1$ and $R_2$, taken together, form —O—; or $R_1$ is the following group (b):

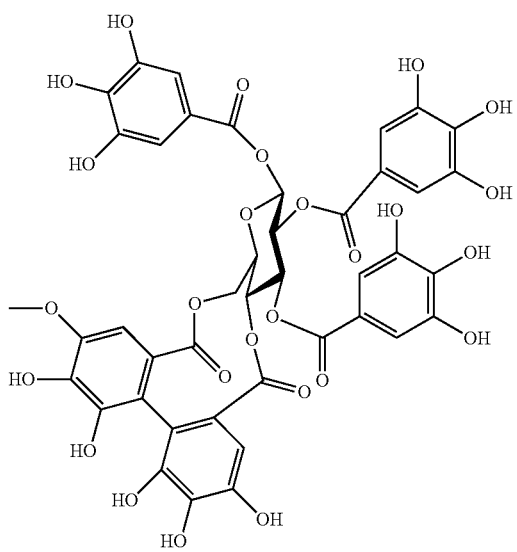

and $R_2$ is —OH}, to a subject in need thereof.

22. The method according to claim 21, wherein the compound in the class of rosacyanins is one or more compounds selected from the group consisting of rosacyanin A1 represented by the following formula:

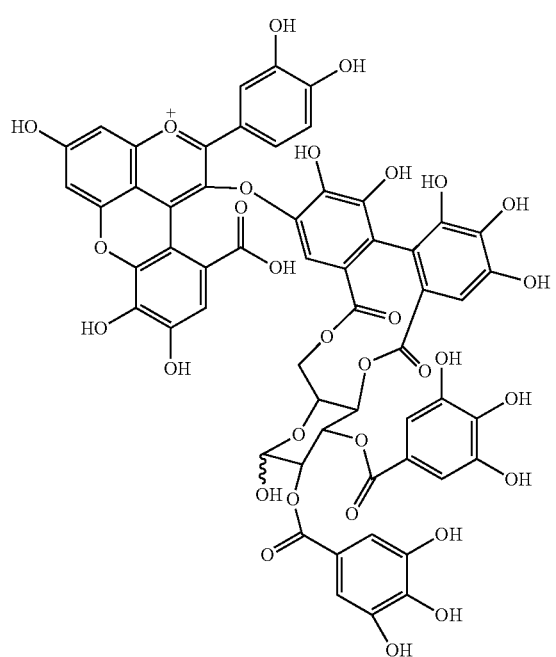

{provided that in this group, the coordination (wavy line) to the hydroxyl group at position 1 of glucose indicates tautomerism of α- and β-forms}, rosacyanin A2 represented by the following formula:

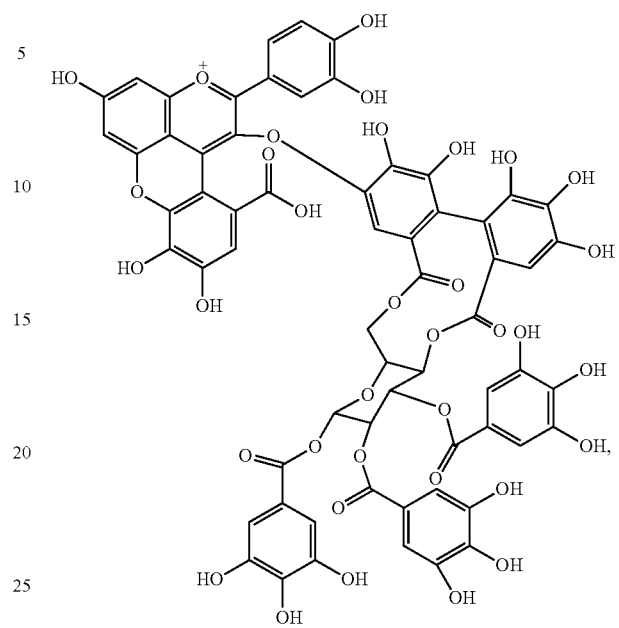

and rosacyanin B represented by the following formula:

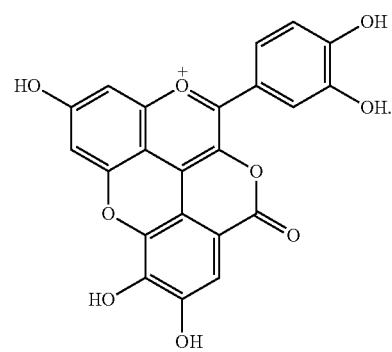

23. The method according to claim 21, wherein the compound in the class of rosacyanins is administered as an extract of a plant of the family Rosaceae that contains the compound in the class of rosacyanins.

24. The method according to claim 23, wherein the plant of the family Rosaceae that contains the compound in the class of rosacyanins is one or more plants of the family Rosaceae as selected from the group consisting of Madame Violet, Purple Rain, Lavande, Manhattan Blue, Chantilly Lace, Blue Moon, Tasogare, Charles de Gaulle, Violet Dolly, Blue Ribbon, Aozora, Lady X, Blue Bajou, and Sterling Silver.

25. The method according to claim 21, wherein the compound in the class of rosadelphins is one or more compounds selected from the group consisting of rosadelphin A1 represented by the following formula:

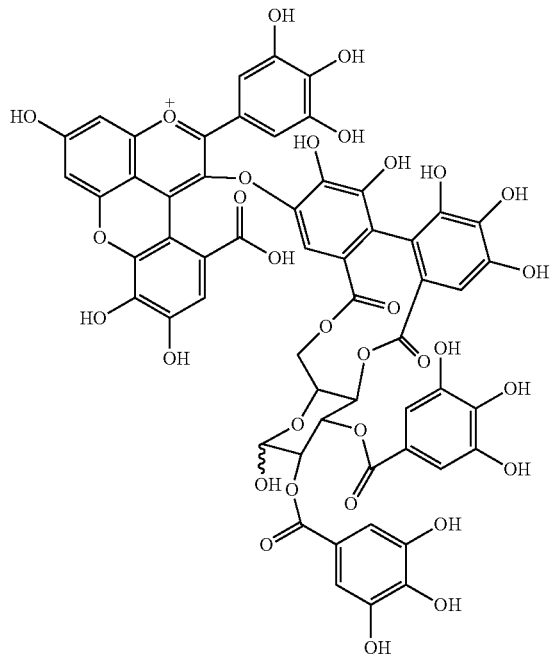

{provided that in this group, the coordination (wavy line) to the hydroxyl group at position 1 of glucose indicates tautomerism of α- and β-forms},
rosadelphin A2 represented by the following formula:

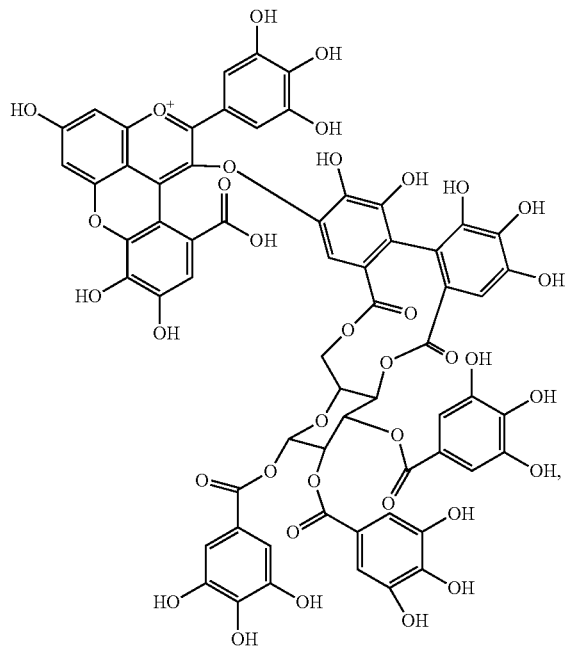 [SMILES: O=C(OC1OC2COC(=O)c3cc(Oc4c(-c5cc(O)c(O)c(O)c5)[o+]c5cc(O)cc6c5c4-c4c(C(=O)O)cc(O)c(O)c4O6)c(O)c(O)c3-c3c(cc(O)c(O)c3O)C(=O)OC2C(OC(=O)c2cc(O)c(O)c(O)c2)C1OC(=O)c1cc(O)c(O)c(O)c1)c1cc(O)c(O)c(O)c1]

and rosadelphin B represented by the following formula:

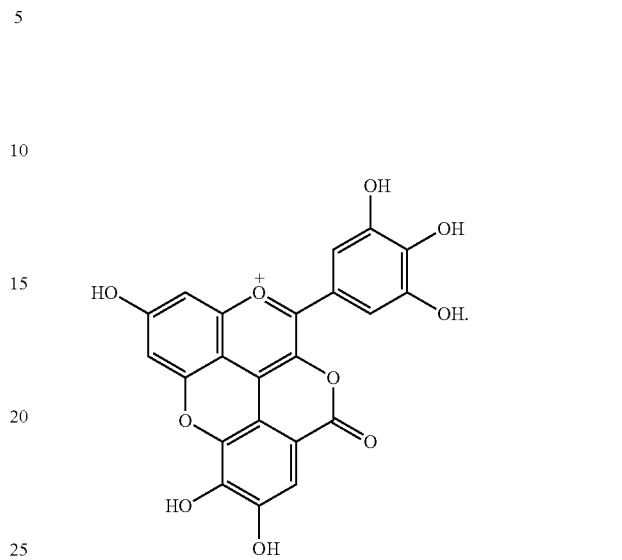

26. The method according to claim 21, wherein the compound in the class of rosadelphins is administered as an extract of a plant of the family Rosaceae that contains the compound in the class of rosadelphins.

27. The method according to claim 26, wherein the plant of the family Rosaceae that contains the compound in the class of rosadelphins is a plant of the family Rosaceae that contains the flavonoid 3', 5'-hydroxylase gene.

28. The method according to claim 21, wherein administration of said one or more compounds suppresses matrix metalloproteinase 1 (MMP-1) production.

29. The method according to claim 21, wherein administration of said one or more compounds promotes collagen synthesis.

30. The method according to claim 21, wherein administration of said one or more compounds is cutaneous administration.

* * * * *